(12) United States Patent
Wang et al.

(10) Patent No.: US 12,198,340 B2
(45) Date of Patent: Jan. 14, 2025

(54) SYSTEM AND METHOD FOR CARDIOVASCULAR RISK PREDICTION AND COMPUTER READABLE MEDIUM THEREOF

(71) Applicant: National Taiwan University, Taipei (TW)

(72) Inventors: Tzung-Dau Wang, Taipei (TW);
Wen-Jeng Lee, Taipei (TW);
Yu-Cheng Huang, Taipei (TW);
Chiu-Wang Tseng, Taipei (TW);
Cheng-Kuang Lee, Taipei (TW);
Wei-Chung Wang, Taipei (TW);
Cheng-Ying Chou, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 340 days.

(21) Appl. No.: 17/804,839

(22) Filed: May 31, 2022

(65) Prior Publication Data
US 2024/0005479 A1    Jan. 4, 2024

(51) Int. Cl.
*G06T 7/00* (2017.01)
*G06T 7/90* (2017.01)
(52) U.S. Cl.
CPC .............. *G06T 7/0012* (2013.01); *G06T 7/90* (2017.01); *G06T 2207/10072* (2013.01); *G06T 2207/30048* (2013.01)

(58) Field of Classification Search
CPC ................ G06T 7/0012; G06T 7/90; G06T 2207/10072; G06T 2207/30048; G06T 2207/30101; G06T 7/11; G06T 2207/20081; G16H 15/00; G16H 30/40; G16H 50/20; G16H 50/30
See application file for complete search history.

(56) References Cited

U.S. PATENT DOCUMENTS 9,968,257 B1 *   5/2018  Burt ..................... A61B 5/0035
2020/0342600 A1 * 10/2020 Sjöstrand ............... A61B 6/032
2023/0086355 A1 *  3/2023 Wichern ................. G10L 25/30
                                                            704/200

\* cited by examiner

*Primary Examiner* — Dhaval V Patel
(74) *Attorney, Agent, or Firm* — HSML P. C.

(57) ABSTRACT

Provided are a system and a method for cardiovascular risk prediction, where artificial intelligence is utilized to perform segmentation on non-contrast or contrast medical images to identify precise regions of the heart, pericardium, and aorta of a subject, such that the adipose tissue volume and calcium score can be derived from the medical images to assist in cardiovascular risk prediction. Also provided is a computer readable medium for storing a computer executable code to implement the method.

16 Claims, 26 Drawing Sheets
(18 of 26 Drawing Sheet(s) Filed in Color)

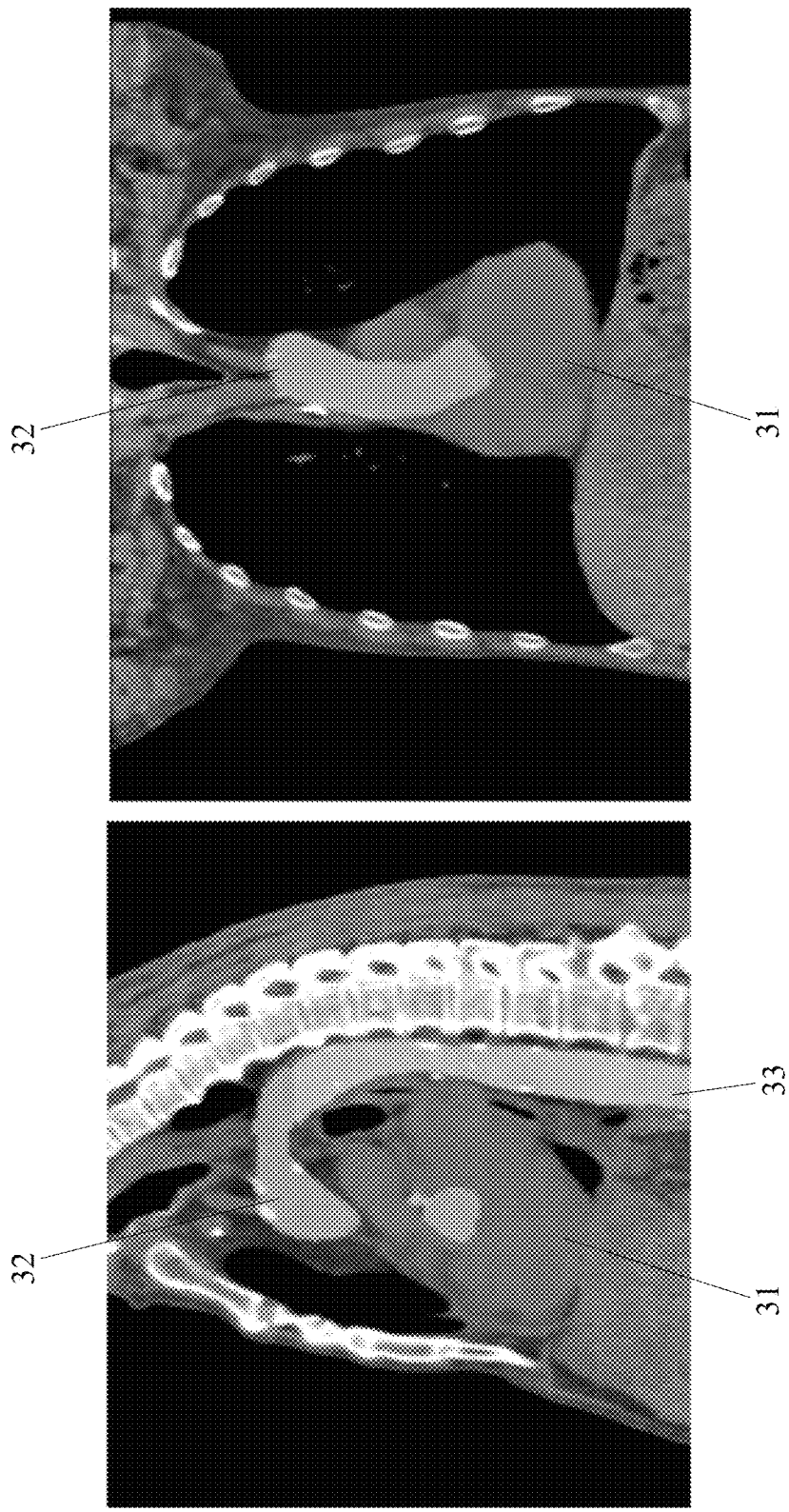

Cadiovascular Combined Risk Calculator

Exam: 20XX/07/12    Accession number: XXX
Patient Name: XXX   Patient ID: XXX
Institute: XX       Sex: F / Age: 67

| Image | Result |
|---|---|
| [CT image] | Calcium quantification<br>Heart: 152<br>Ascending aorta: 18<br>Descending aorta: 307<br>Fat score: 150.723<br><br>Survival analysis<br><br>\| Year \| Event \| Probability \|<br>\|---\|---\|---\|<br>\| 1.0 \| Rehospitalization / Mortality \| 24.4% \|<br>\| 1.5 \| Rehospitalization / Mortality \| 34.2% \|<br>\| 2.0 \| Rehospitalization / Mortality \| 41.0% \|<br><br>For study only. |

Date of Creation:20XX/10/22
Creator: Admin
Version Info:
  Calcium Quantification: Ver.XXX
  Automatic Segmentation: Ver.XXX
  Survival Analysis: Ver.XXX

FIG. 9

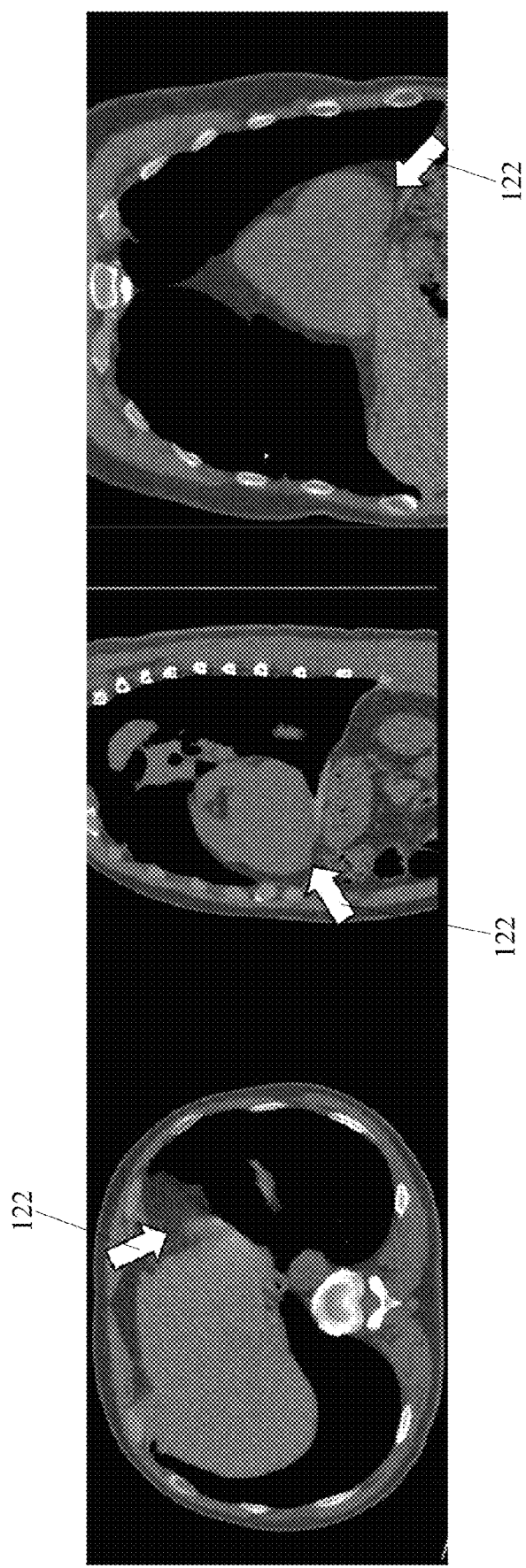

SYSTEM AND METHOD FOR CARDIOVASCULAR RISK PREDICTION AND COMPUTER READABLE MEDIUM THEREOF

TECHNICAL FIELD

The present disclosure relates to medical image analysis, and more particularly to system and method for cardiovascular risk prediction and computer readable medium thereof.

DESCRIPTION OF RELATED ART

In the field of medical image analysis, quantifying calcification in heart/aorta and adipose tissues surrounding or within the heart/aorta, like epicardial adipose tissue (EAT), are important predictors of future cardiovascular risk. In particular, quantification of calcification in heart/aorta may reflect the amount of calcified plaques in aorta and coronary artery, and quantification of EAT within the pericardium may reflect regional thickness of fat surrounding coronary arteries which may confer inflammation and/or coronary atherosclerosis.

Existing techniques for identifying the above variables, such as invasive diagnostic tests (e.g., cardiac catheterization), may be useful for deriving accurate lesion identification, but they are associated with additional surgical risk and medical expenses. Therefore, non-invasive approaches for diagnosing cardiovascular risks are of high value in the market.

Based on the above, there is an unmet need in the art to utilize artificial intelligence in segmenting regions of heart, aorta and/or pericardium from non-contrast or contrast medical images and deriving EAT and calcium score therefrom for the sake of cardiovascular risk prediction.

SUMMARY

In view of the foregoing, the present disclosure provides a system for cardiovascular risk prediction, comprising: a segmentation module configured to segment a region from a medical image; and an extraction module configured to extract an analysis result from the region of the medical image.

The present disclosure also provides a method for cardiovascular risk prediction, comprising: configuring a segmentation module to segment a region from a medical image; and configuring an extraction module to extract an analysis result from the region of the medical image.

In at least one embodiment of the present disclosure, the medical image is a non-contrast computed tomography image. In at least one embodiment of the present disclosure, the medical image is a contrast medical image.

In at least one embodiment of the present disclosure, the segmentation module is implemented with a machine learning model to segment the region from the medical image, and the machine learning model has a network architecture comprising an encoder part, a decoder part, an attention mechanism, and a variational auto-encoder decoder branch.

In at least one embodiment of the present disclosure, the attention mechanism is configured to highlight salient features passed through skip connections between the encoder part and the decoder part, and the variational auto-encoder decoder branch is configured to reconstruct the medical image based on features from endpoint of the encoder part during training of the machine learning model.

In at least one embodiment of the present disclosure, further comprising a model training module configured to provide training to the machine learning model through steps of: pre-processing a training data into a predetermined consistency; augmenting the training data by performing random cropping, random spatial flipping and/or random scaling or shifting of intensity on the training data; training the machine learning model using the training data; and validating a training result of the machine learning model using a loss function.

In at least one embodiment of the present disclosure, the training data is generated via labeling a non-contrast or contrast medical image manually and/or with assistance of an auxiliary annotation model.

In at least one embodiment of the present disclosure, the analysis result comprises an adipose tissue volume of the region, and the extraction module comprises a fat extraction unit configured to quantify the adipose tissue volume within a pericardium in the region through steps of: calculating a Hounsfield unit value for the pericardium based on an attenuation coefficient under computed tomography; defining a range of positive and negative standard deviation for the Hounsfield unit value on a basis of noise tolerance; and determining the adipose tissue volume within the pericardium based on the range. In some embodiments, the adipose tissue may be epicardial adipose tissue, but the present disclosure is not limited thereto.

In at least one embodiment of the present disclosure, the analysis result comprises a calcium score of the region, and wherein the extraction module comprises a calcium extraction unit configured to quantify the calcium score of a heart or an aorta from the region through steps of: identifying a calcium region from the region based on a cut point defined by an Agatston score; capturing the calcium regions as a 3D image; analyzing the 3D image by a classifier to determine a classification of the calcium region; assigning a calcium score for the calcium region; and generating a heatmap to illustrate the calcium region and the calcium score.

In at least one embodiment of the present disclosure, further comprising a pre-processing module configured to pre-process the medical image into a predetermined consistency through steps of: resampling a 3D volume of the medical image into a spacing of 2×2×2 mm; normalizing an intensity of the 3D volume into unit standard deviation with zero mean; and converting the 3D volume into form of a channel-first matrix.

In at least one embodiment of the present disclosure, further comprising an output module configured to present a cardiovascular risk prediction score based on the analysis result.

The present disclosure further provides a computer readable medium, which stores a computer executable code, and the computer executable code implements the method mentioned above after being executed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 5A to 5E are schematic diagrams illustrating segmented regions from medical image in accordance with the present disclosure.

FIG. 9 is a schematic diagram illustrating a report of cardiovascular risk prediction in accordance with the present disclosure.

FIGS. 12A-1 to 12D-3 are schematic diagrams illustrating a process of manually labeling heart for training data.

FIGS. 13A to 13G-2 are schematic diagrams illustrating a process of manually labeling aorta for training data.

DETAILED DESCRIPTION OF THE EMBODIMENTS

Figure 1:
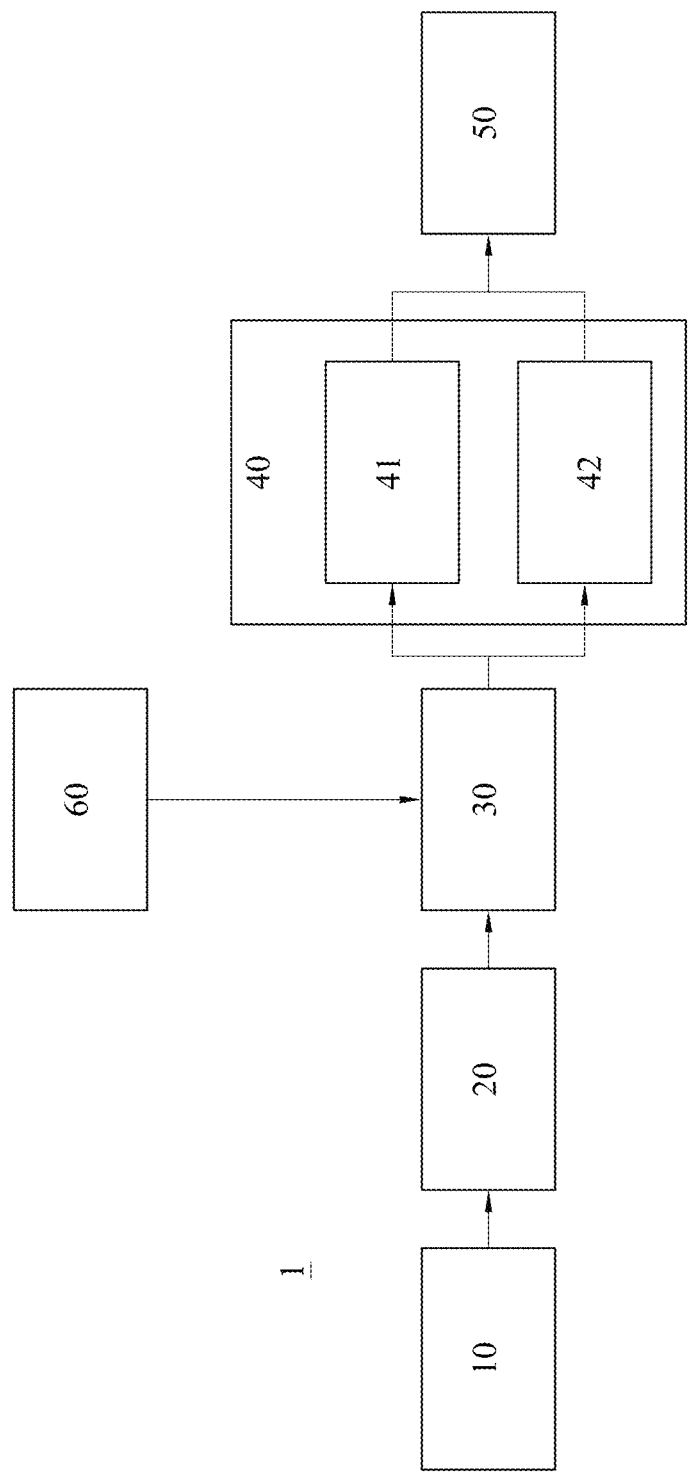
FIG. 1 is a schematic diagram illustrating a system for cardiovascular risk prediction in accordance with the present disclosure.

The following embodiments are provided to illustrate the present disclosure in detail. A person having ordinary skill in the art can easily understand the advantages and effects of the present disclosure after reading the disclosure of this specification, and also can implement or apply in other different embodiments. Therefore, it is possible to modify and/or alter the following embodiments for carrying out this disclosure without contravening its scope for different aspects and applications, and any element or method within the scope of the present disclosure disclosed herein can combine with any other element or method disclosed in any embodiments of the present disclosure.

The proportional relationships, structures, sizes and other features shown in accompanying drawings of this disclosure are only used to illustrate embodiments describe herein, such that those with ordinary skill in the art can read and understand the present disclosure therefrom, of which are not intended to limit the scope of this disclosure. Any changes, modifications, or adjustments of said features, without affecting the designed purposes and effects of the present disclosure, should all fall within the scope of the technical content of this disclosure.

As used herein, sequential terms such as "first," "second," etc., are only cited in convenience of describing or distinguishing limitations such as elements, components, structures, regions, parts, devices, systems, etc. from one another, which are not intended to limit the scope of this disclosure, nor to limit spatial sequences between such limitations. Further, unless otherwise specified, wordings in singular forms such as "a," "an" and "the" also pertain to plural forms, and wordings such as "or" and "and/or" may be used interchangeably.

As used herein, the terms "subject," "individual" and "patient" may be interchangeable and refer to an animal, e.g., a mammal including the human species. The term "subject" is intended to refer to both the male and female gender unless one gender is specifically indicated.

As used herein, the terms "comprise," "comprising," "include," "including," "have," "having," "contain," "containing," and any other variations thereof are intended to cover a non-exclusive inclusion. For example, when describing an object "comprises" a limitation, unless otherwise specified, it may additionally include other elements, components, structures, regions, parts, devices, systems, steps, or connections, etc., and should not exclude other limitations.

As used herein, the phrase "at least one," in reference to a list of one or more elements, should be understood to mean at least one element selected from any one or more of the elements in the list of elements, but not necessarily including at least one of each and every element listed within the list of elements and not excluding any combinations of elements in the list of elements. This definition also allows that elements may optionally be present other than the elements identified within the list of elements to which the phrase "at least one" refers, whether related or unrelated to those elements identified. Thus, as a non-limiting example, "at least one of A and B" (or, equivalently, "at least one of A or B," or, equivalently, "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements).

As used herein, the terms "one or more" and "at least one" may have the same meaning and include one, two, three, or more.

Referring to FIG. 1, a system 1 of the present application for cardiovascular risk prediction is disclosed. In at least one embodiment, the system 1 mainly comprises an image acquisition module 10, a pre-processing module 20, a segmentation module 30, an extraction module 40, an output module 50 and a model training module 60. The arrows denoted between said elements of the system 1 represent the operation relationships and information transmission direction therebetween, which can be realized in any suitable wired or wireless means.

In some embodiments, the image acquisition module 10 may be coupled to or implanted in a scanning device to acquire medical image of a subject (e.g., a patient). In preferred embodiments, the scanning device is a computed tomography (CT) scanner provided by Philips (Brilliance iCT, Brilliance CT), General Electronics (Lightspeed VCT, Revolution CT), Siemens (Somation Definition AS), Canon (Aquilion PRIME), or the like, and the medical image obtained is a non-contrast CT image. In embodiments described herein, the image acquisition module 10 may also be coupled to or implanted in a picture archiving and communication system (PACS) installed within arbitrary hospital, such that medical image stored by the PACS may be associated by the image acquisition module 10 for later processing in the system 1. In further embodiments, the image acquisition module 10 may also accept medical images of the subject via manual means by providing an interactive interface for uploading/importing of medical images. However, the scanning device, medical image, and the image acquisition module 10 discussed above may also be realized in other suitable formats, thus is not meant to limit scope of the present disclosure. A detailed functionality of the image acquisition module 10 will be further described later in this disclosure.

In some embodiments, the pre-processing module 20 is configured to maintain consistency of medical image obtained by the image acquisition module 10 before analysis procedure later performed in the system 1. In embodiments described herein, the tasks performed by the pre-processing module 20 may include, but not limited to, resampling, normalization, and conversion of the medical images. A detailed functionality of the pre-processing module 20 will be further described later in this disclosure.

In some embodiments, the segmentation module 30 is configured to segment regions of heart, pericardium and/or aorta from a given medical image (after pre-processed by the pre-processing module 20) for further analysis of cardiovascular risk prediction. In embodiments described herein, the segmentation module 30 is implemented with a machine learning model configured to perform tasks of segmentation. The machine learning model may be developed on a basis of algorithms such as decision tree, convolutional neural network (CNN), recurrent neural network (RNN), and the like, or any combination thereof, of which the present disclosure is not limited thereto. A detailed functionality of the segmentation module 30 will be further described later in this disclosure.

In some embodiments, the extraction module 40 is configured to extract an analysis result from the medical image after segmentation. In embodiments described herein, the extraction module 40 comprises a fat extraction unit 41 configured to calculate an adipose tissue volume from said medical image, and a calcium extraction unit 42 configured to calculate a calcium score from said medical image. It should be noted that the extraction module 40 may also comprise other units for extracting other information from the medical image to assist in cardiovascular risk prediction, of which the present disclosure is not limited thereto. A detailed functionality of the extraction module 40 will be further described later in this disclosure.

In some embodiments, the output module 50 is configured to output an analysis result regarding the cardiovascular risk of a subject after analysis of the medical image. In embodiments described herein, the analysis result may be realized in form of a report, which indicates information of segmented regions, adipose tissue volume, calcium score, etc. from said medical image. However, other forms for presenting an analysis result may also be utilized and should not be restrictive to the scope of the present disclosure. A detailed functionality of the output module 50 will be further described later in this disclosure.

In some embodiments, the model training module 60 is configured to provide training of the machine learning model before deploying to the segmentation module 30. In embodiments described herein, the training of the machine learning model is performed based on concepts of the federated learning and/or adaptive learning, such that the machine learning model may keep refining its segmentation accuracy based on updated medical image and parameter settings gathered from clinical practice of different institutions and/or scanning devices even if the machine learning model is already deployed for practical use. A detailed functionality of the model training module 60 will be further described later in this disclosure.

In some embodiments, the elements of the system 1 may be individually realized as any suitable computing device, apparatus, program, system, or the like, but the present disclosure is not limited thereto. In some embodiments, any two or more of the image acquisition module 10, the pre-processing module 20, the segmentation module 30, the extraction module 40, the output module 50 and the model training module 60 may be integrated instead of being realized as distinct units. In some embodiments, said elements may also be realized in a cloud computing environment. Nevertheless, without straying from the operation philosophy of the present disclosure, the configuration of said elements of the system 1 may be realized in any suitable forms and should not be restrictive to the scope of the present disclosure.

Figure 2:
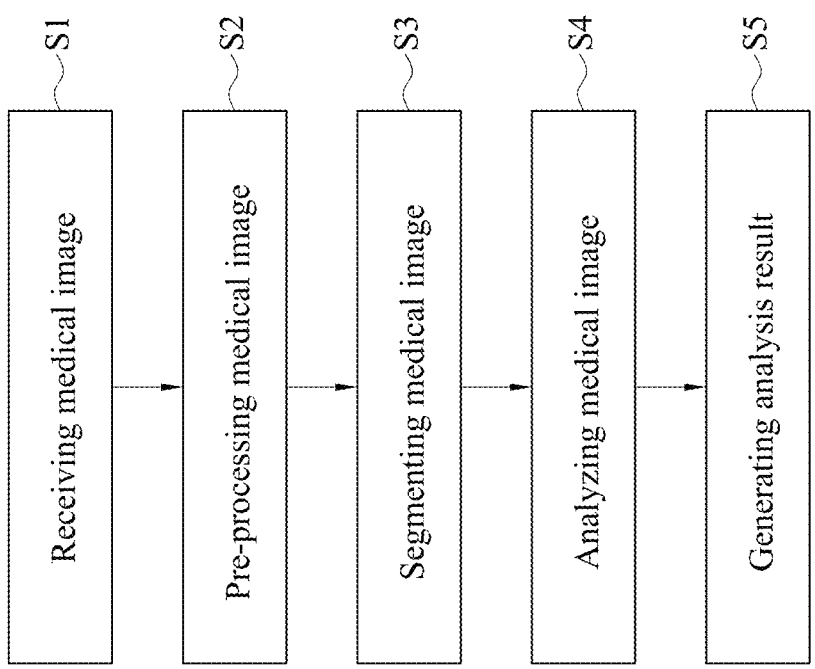
FIG. 2 is a flow chart illustrating steps for cardiovascular risk prediction in accordance with the present disclosure.
Figure 3B:
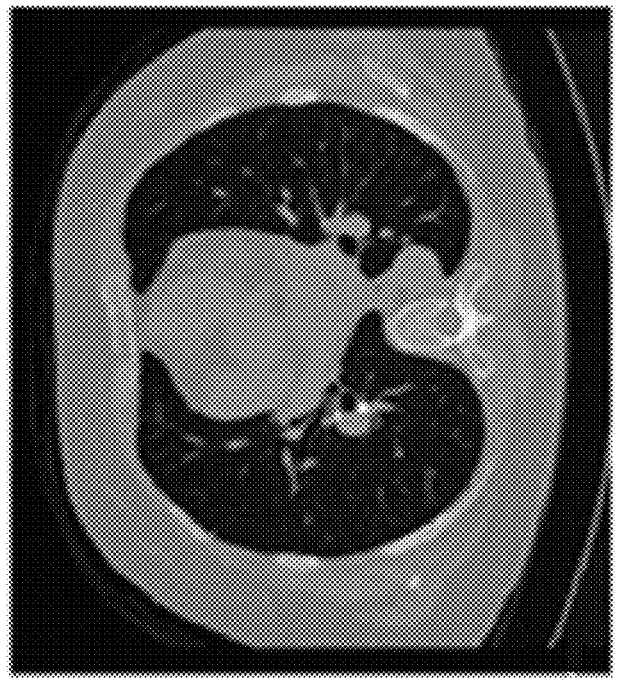
FIGS. 3A and 3B are schematic diagrams illustrating images taken by scanning devices of different imaging capabilities in accordance with the present disclosure.
Figure 3A:
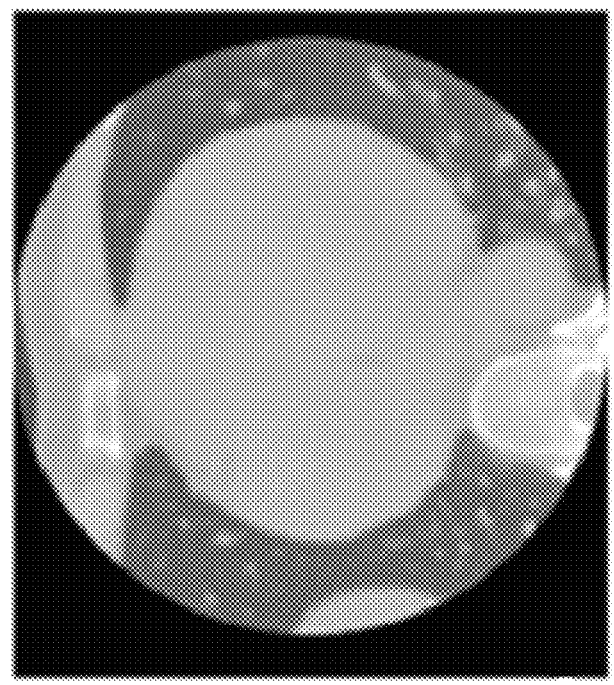

Referring to FIG. 2, a flow chart describing steps for cardiovascular risk prediction utilizing elements of the system 1 is disclosed, where FIGS. 3A-3B, 4A-4B, 5A-5E and 6-9 are also cited to illustrate execution details for each step by reference. It should be understood that the steps illustrated in FIG. 2 are configured to execute on a basis that the machine learning model of the segmentation module 30 is fully trained and ready for practical use. However, the training process of the machine learning model may also be executable in steps of FIG. 2 under the concept of the adaptive learning, and thus will not interfere said steps of FIG. 2.

At step S1, one or more medical images are obtained by the image acquisition module 10 (e.g., from scanning device and/or PACS). In embodiments described herein, the image acquisition module 10 is configured to receive medical images on digital imaging communications in medicine (DICOM) standards, and a graphical user interface (GUI) may be provided by the image acquisition module 10 for user to manually or automatically upload and import medical images therefrom. As explained above, the medical images are not limited to computed tomography (CT) images, but also may be magnetic resonance imaging (MRI) images, single photon emission computed tomography (SPECT) images, positron tomography (PET) images, or the like, of which the present disclosure is not limited thereto. Further, due to the region of interest for analysis purpose, the medical image being obtained should contain at least area around the heart of a subject (e.g., "chest CT image"), but content of the medical images may vary depending on imaging capabilities of the scanning device (e.g., see FIGS. 3A and 3B, where a scanning device of hospital A may only image the heart of the subject, while a scanning device of hospital B may image an entire thorax of the subject), of which the present disclosure is also not limited thereto. In alternative embodiments, a filter mechanism may be implemented by the image acquisition module 10 to ensure the medical images are indeed associated with region of interest of the subject before analysis.

At step S2, the one or more medical images are pre-processed by the pre-processing module 20 into a predetermined consistency before analysis. In some embodiments described herein, the pre-processing of the medical images comprises the following steps: resampling three-dimensional (3D) volume of the medical images into a spacing of 2×2×2 mm; normalizing intensity of resampled 3D volume of the medical images into unit standard deviation with zero mean (i.e., mean is zero and standard deviation is one); and converting the normalized 3D volume of the medial images into the form of a channel-first matrix. In at least one embodiment, said resampling of 3D volume of the medial images may avoid out-of-memory during later processing of the segmentation module 30. In at least one embodiment, said normalizing intensity of the resampled 3D volume of the medical images may help medical images from different scanning devices consistent, hence a better segmentation result for the segmentation module 30 can be obtained. In at least one embodiment, said converting the normalized 3D volume of the medical images may help speed up the operation speed during later processing of the segmentation module 30. After pre-processing of the medical images, they can act as input for the segmentation module 30 for further processing.

At step S3, the one or more medical images are segmented by the machine learning model of the segmentation module 30 to identify regions of heart, pericardium and aorta of the subject. In embodiments described herein, an output from the machine learning model of the segmentation module 30 is a medical image of a subject labeled with regions of heart, pericardium, ascending aorta, and descending aorta, which will be respectively processed to determine an adipose tissue volume and calcium score therefrom in later processing.

Figure 4A:
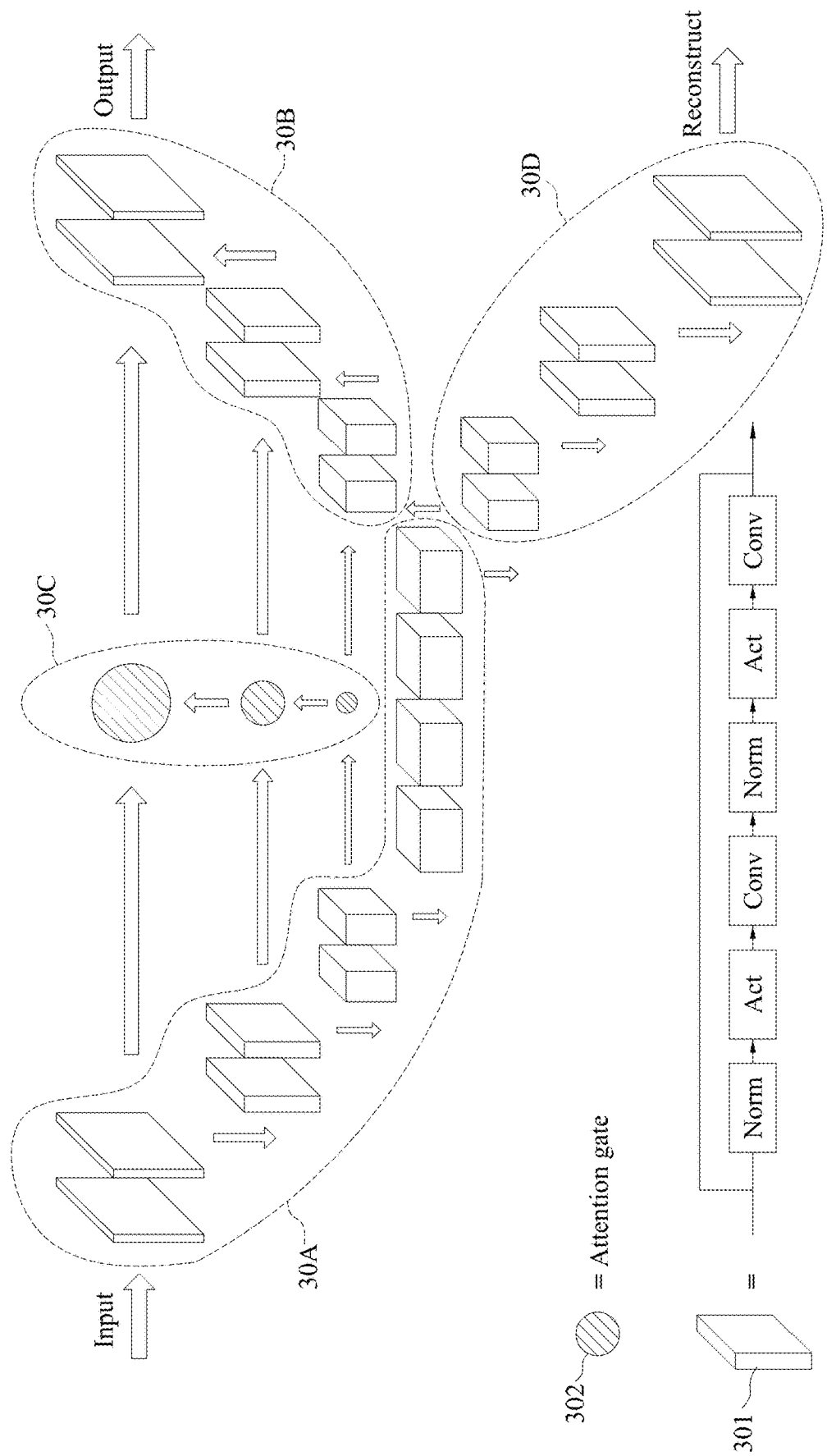
FIGS. 4A and 4B are schematic diagrams illustrating network architecture of a machine learning model in accordance with the present disclosure.

Referring to FIG. 4A, the network architecture of the machine learning model used herein is disclosed, which comprises an encoder part 30A, a decoder part 30B, an attention mechanism 30C, and a variational auto-encoder (VAE) decoder branch 30D. From the network architecture as illustrated, it is shown that the machine learning model is based on a U-Net structure, and each of the residual convolution blocks 301 therefrom is stacked by 6 operations, i.e., group-normalization (denoted as "Norm" in FIG. 4A), rectified linear unit (ReLU) (denoted as "Act" in FIG. 4A), convolution (denoted as "Conv" in FIG. 4A), group-normalization, ReLU, and convolution, with a shortcut connecting and an initial 16 filters. In at least one embodiment, the encoder part 30A is configured to progressively downsizing (see the down arrows of the encoder part 30A) image dimension of the input (medical images) while simultaneously increasing feature size of the input during feature extraction of the input. In at least one embodiment, the decoder part 30B is configured to progressively reducing feature size while simultaneously up-sizing (see the up arrows of the decoder part 30B) image dimension of features from endpoint of the encoder part 30A level-by-level until an output having a same spatial size of the input is produced. In at least one embodiment, the attention mechanism 30C is configured to highlight salient features that are passed through the skip connections (see the horizontal arrows around the attention mechanism 30C) between the encoder part 30A and the decoder part 30B. In at least one embodiment, the variational auto-encoder (VAE) decoder branch 30D is configured to reconstruct the input (medical image) based on features from endpoint of the encoder part 30A following a same architecture of the decoder part 30B, which is useful for adding additional guidance and regularization to the encoder part 30A during training if training data is limited.

Figure 4B:
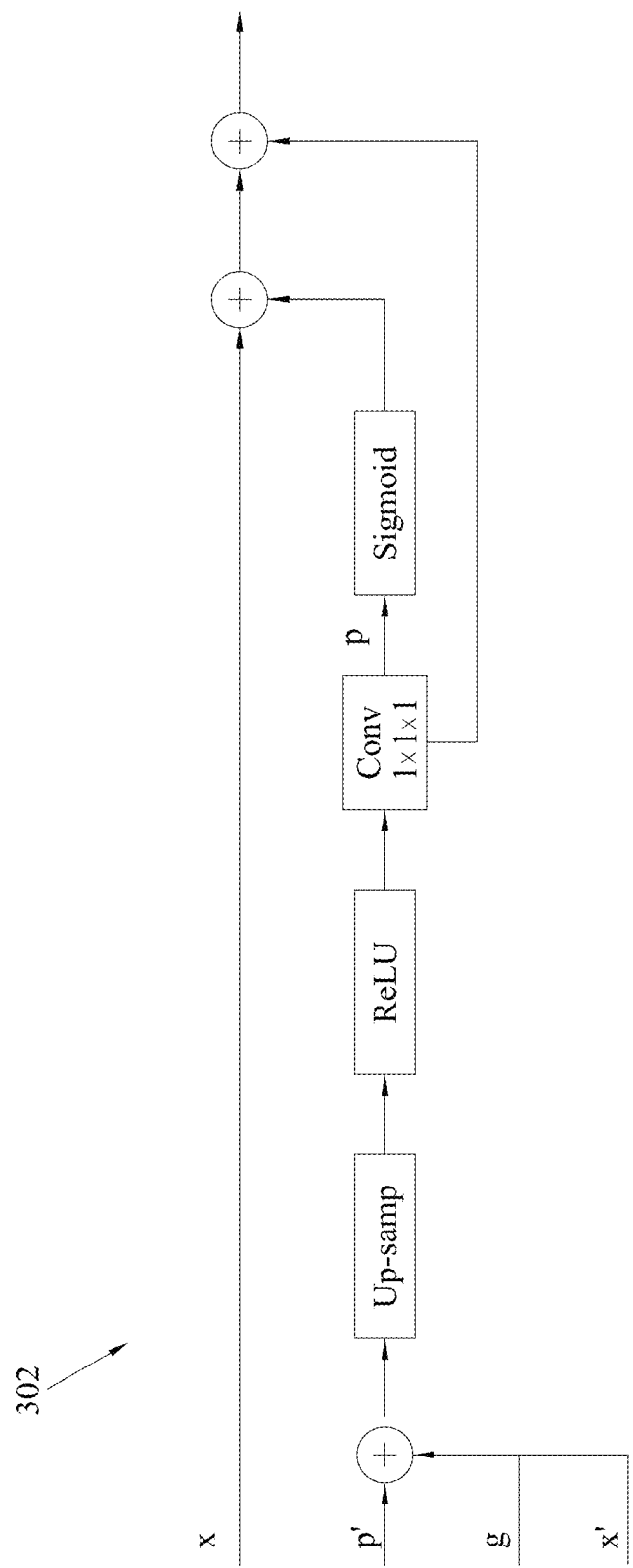

Referring to FIGS. 4A and 4B, the attention mechanism 30C comprises a plurality of attention gates 302 corresponding in levels of decoder part 30B and stacked by operations of up-sampling, ReLU, convolution, and Sigmoid, where a previous attention logit p' carrying information learned from a previous layer, a gating signal g carrying contextual information from a previous coarser scale, and a previous skipped feature x' (i.e., skipped feature x passed through two residual convolution blocks 301 at corresponding level of the encoder part 30A) are considered by each attention gate 302 to produce an attention logit p before entering a next attention gate 302 and/or concatenated with the decoder part 30B for output.

Figure 5C:
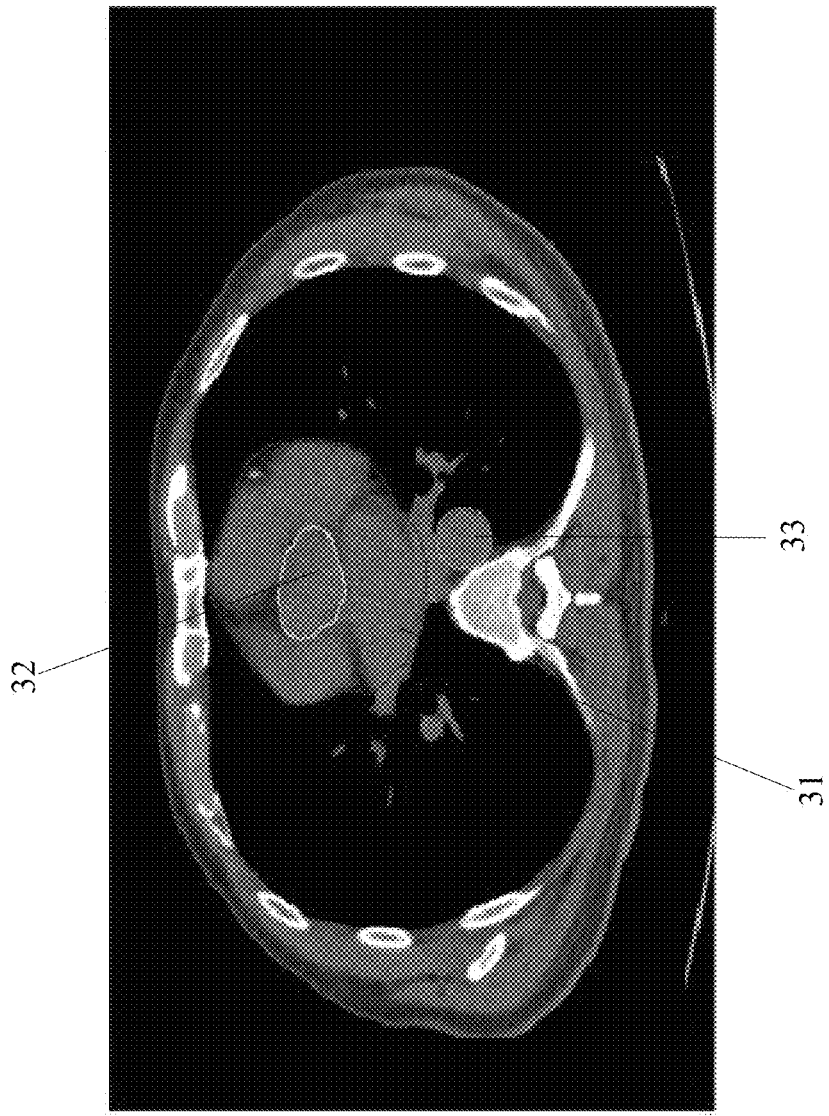
Figure 5D:
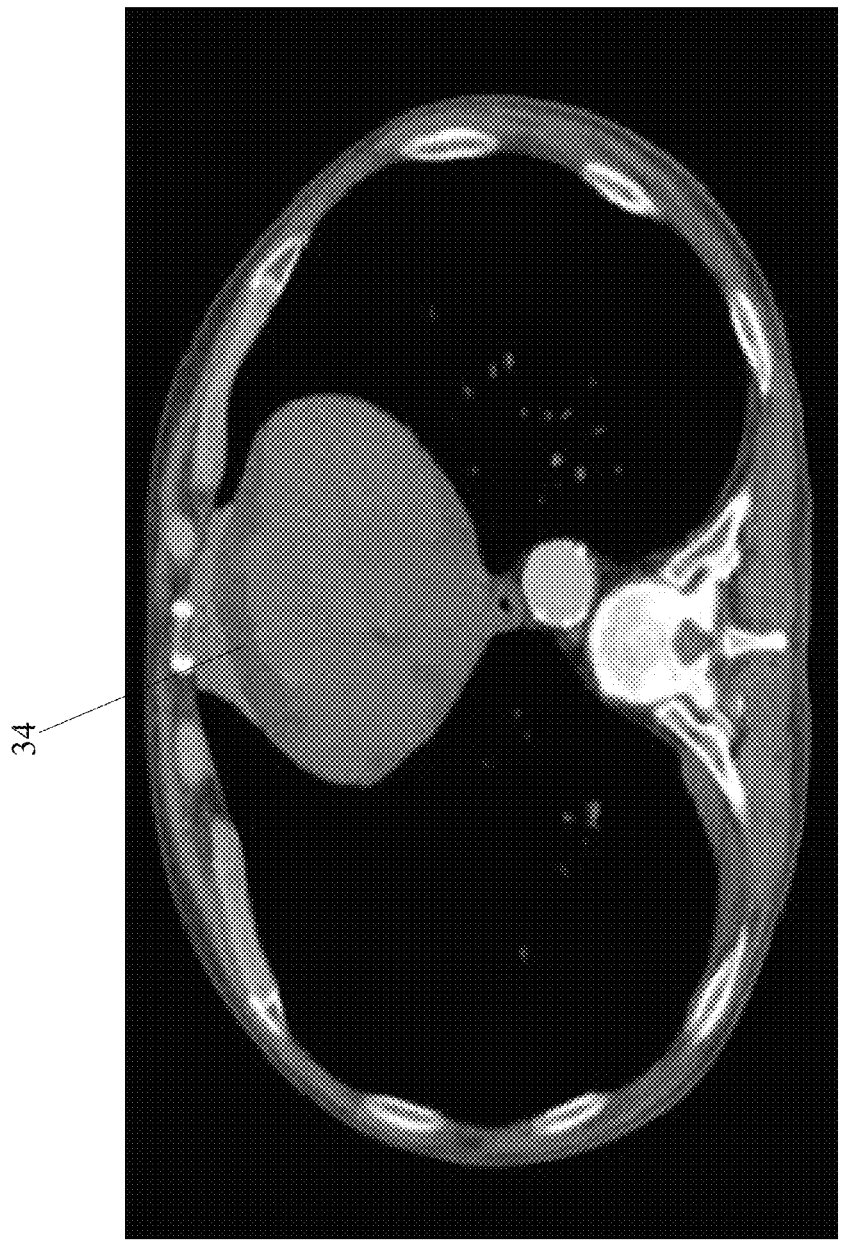
Figure 5E:
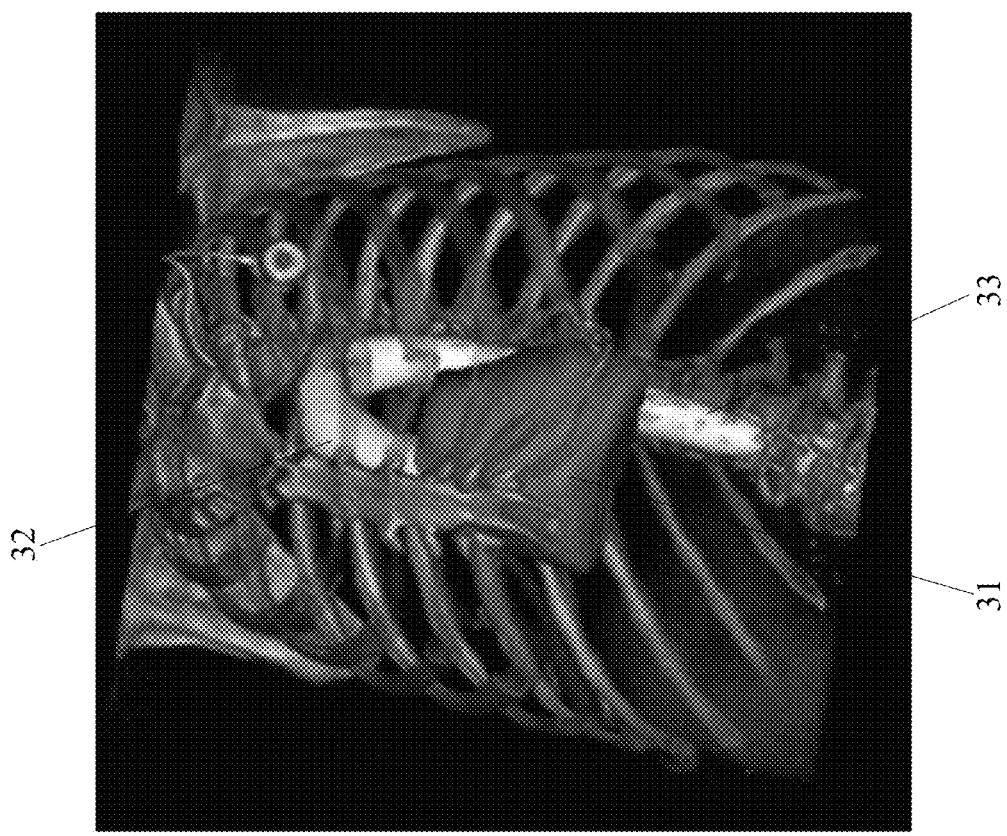

Referring to FIGS. 5A-5E, examples of segmentation result of medical images processed by the segmentation module 30 are shown, where FIGS. 5A, 5B and 5C show segmented regions of the pericardium and heart 31, ascending aorta 32, and descending aorta 33 presented in the two-dimensional (2D) view observed from the sagittal plane, coronal plane, and horizontal plane of the subject, respectively; FIG. 5D shows segmented regions of the pericardium 34 presented in the 2D view observed from the horizontal plane of the subject; and FIG. 5E shows segmented regions of the pericardium and heart 31, ascending aorta 32, and descending aorta 33 presented in the 3D view of the thorax of the subject.

At step S4 in FIG. 2, the one or more medical images are analyzed by the extraction module 40 to extract an adipose tissue (e.g., EAT) volume and a calcium score based on segmentation results. In the embodiments described herein, the extraction module 40 is configured to orderly exclude insignificant parts (e.g., vertebra and sternum) from the medical images, and then quantify said adipose tissue volume and calcium score (e.g., via the fat extraction unit 41 and the calcium extraction unit 42) based on a Hounsfield unit (HU) value of the segmented regions presented in the medical images.

Figure 6:
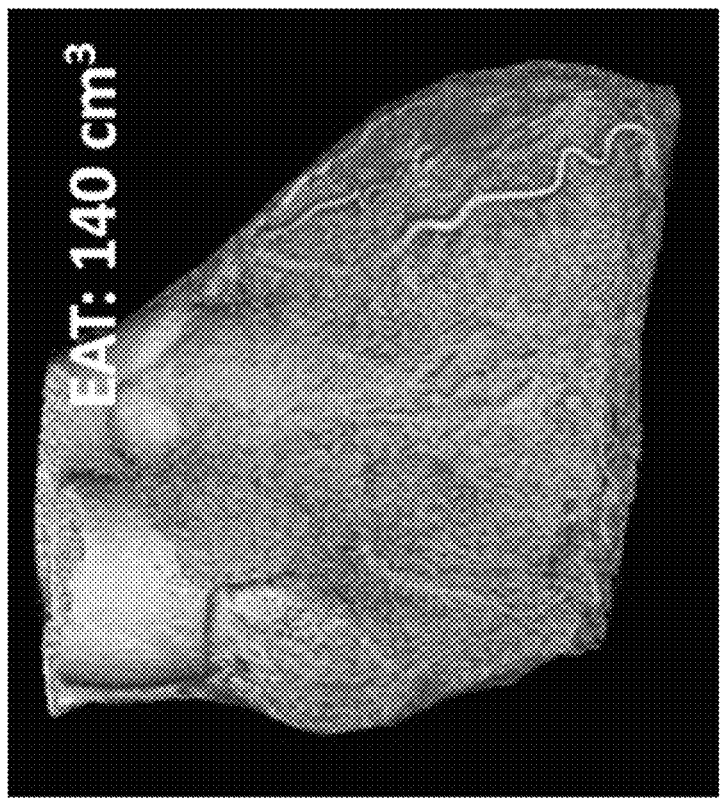
FIG. 6 is a schematic diagram illustrating epicardial adipose tissue (EAT) extracted from medical image in accordance with the present disclosure.

In at least one embodiment, the fat extraction unit 41 is configured to quantify EAT volume from the medical images by: calculating a HU value for the pericardium segmented by the segmentation module 30 based on an attenuation coefficient (e.g., the attenuation coefficient of water, air, and/or calcium) under computed tomography; defining a range of the positive and negative standard deviation for said HU value on a basis of noise tolerance; and determining EAT volume and position within the pericardium based on said range. An example of EAT volume and position extracted by the fat extraction unit 41 is shown in FIG. 6, where a position of EAT is presented as dots on the pericardium, and a volume of EAT being extracted is 140 cm$^3$. In some embodiments, different electron energies of X-ray during scanning may cause different measured attenuations of water, air, and/or calcification, and the algorithm of the present disclosure can perform calibration according to the parameters of the electron energies to obtain a more accurate calcium score or the classification thereof.

Figure 7:
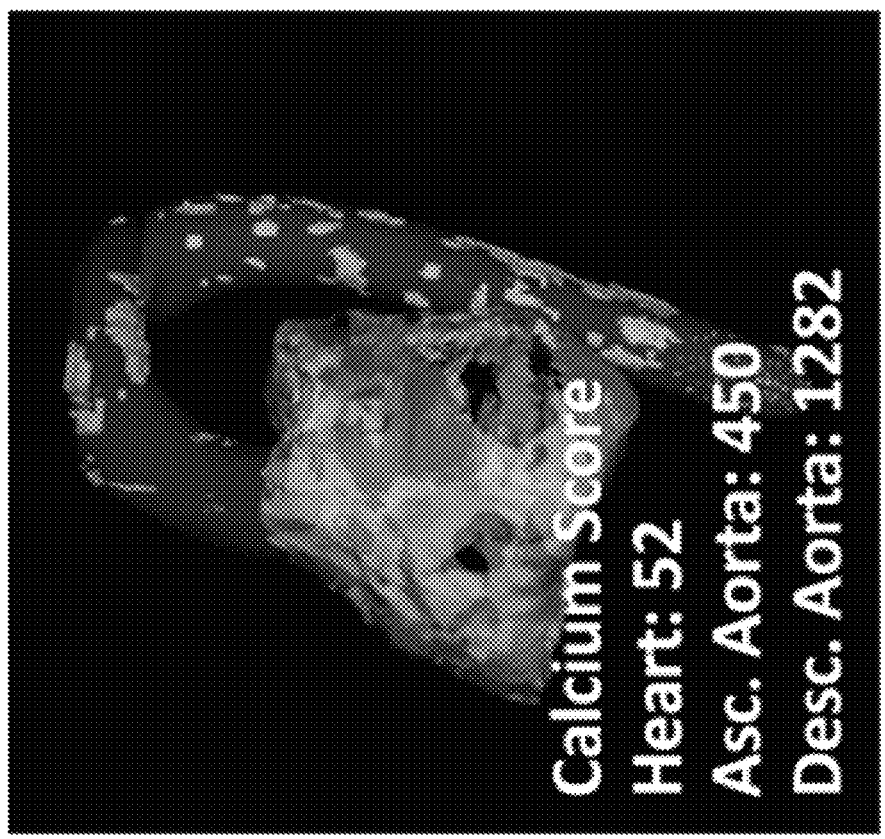
FIG. 7 is a schematic diagram illustrating calcium score extracted from medical image in accordance with the present disclosure.

In at least one embodiment, the calcium extraction unit 42 is configured to quantify a calcium score from the medical images by: identifying one or more calcium regions from segmented regions on the medical images based on a cut point defined by an Agatston score of 130 HU; capturing the calcium regions as a plurality of 3D images; analyzing the plurality of 3D images by a classifier (e.g., a DenseNet) to classify the calcium regions, where classification of the calcium regions may include but not limited to those described in Table 1 below (where beam columns represent field of categories, left columns represent major categories for said field of categories, and right columns represent sub-categories for said major categories); assigning a calcium score for each of the calcium regions; and generating a heatmap (e.g., via a Gradient-weighted Class Activation Mapping technique) to illustrate calcium regions and their corresponding calcium scores. An example of calcium regions and corresponding calcium scores extracted by the calcium extraction unit 42 is shown in FIG. 7, where regions of calcium regions are presented as colored regions on the heart, ascending aorta, and descending aorta, of which the corresponding calcium score from said regions are 52, 450, and 1282, respectively.

TABLE 1

Categories of calcium regions identified by the classifier.

Categories of Natural Calcium

| | |
|---|---|
| Coronary Artery | Left Main (LM) |
| | Left Anterior Descending (LAD) |
| | Left Circumflex (LCx) |
| | Right Coronary Artery (RCA) |
| | Posterior Descending Artery (PDA) |
| Aorta | Ascending Aorta |
| | Aorta Arch |
| | Descending Aorta |
| Valve | Aortic Valve |
| | Pulmonary Valve |
| | Bicuspid Valve |
| | Tricuspid Valve |
| Other Vessels | N/A |
| Other | Trachea |
| | Lymph Node |
| | Artifact |
| Pericardium | N/A |
| Myocardium | N/A |

Categories of Medical Equipment

| | |
|---|---|
| Surgical Material | Nail, clip, and other high density material |
| Cardiovascular Implantable Electronic Device (CIED) | Wire Screw |
| Catheter | NasoGastric (NG) |
| | Central Venous Catheter (CVC) |
| | Port-A-Cath (Port-A) |
| Coronary Stent | N/A |

Categories of Contrast
Categories of Bone and Noise (no extraction is needed)

Figure 8:
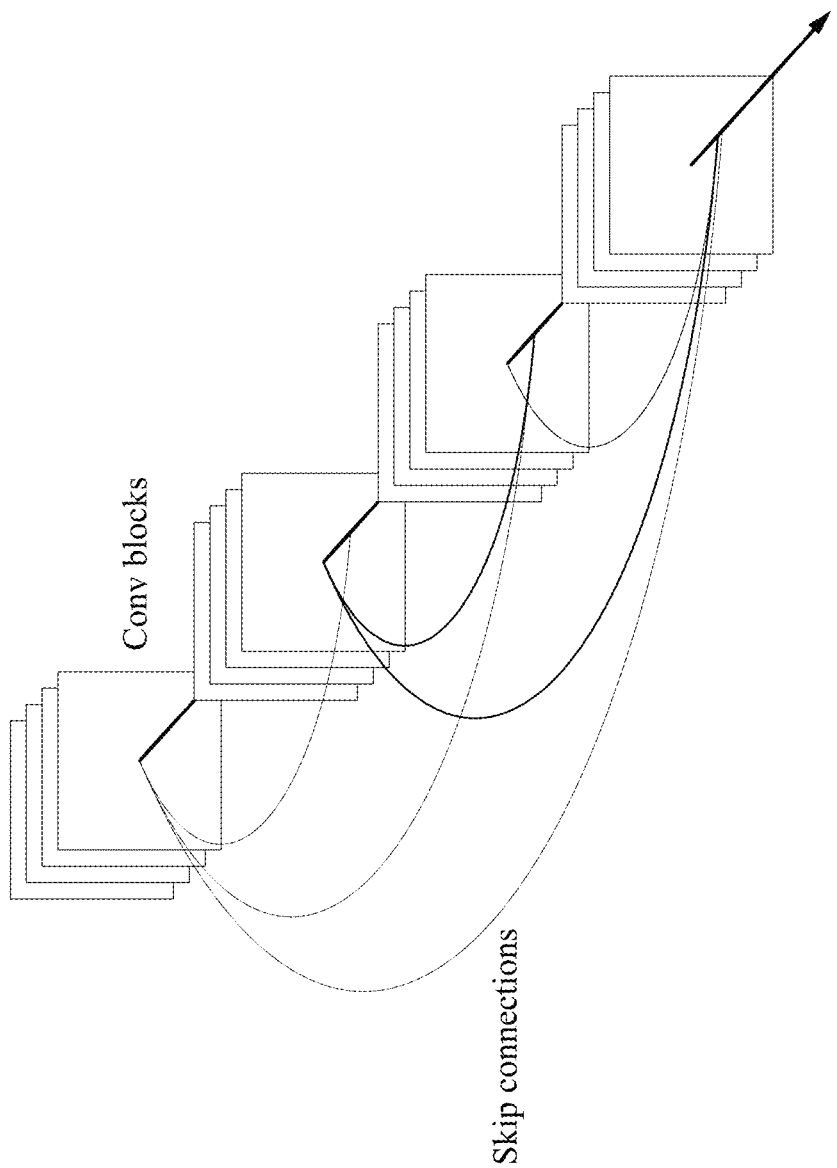
FIG. 8 is a schematic diagram illustrating network architecture of a classifier for classifying calcium regions in accordance with the present disclosure.

Referring to FIG. 8, the classifier utilized by the calcium extraction unit 42 is developed based on network architecture, where convolution blocks within the neural network of the classifier is designed to interconnect with each other (e.g., via skip connections), such that an optimal transmission route may be learned by the classifier for efficiently determining calcium regions from the medical images. In the embodiments described herein, the neural network of the classifier is constructed with a total of 121 layers, but the number of layers of the neural network for the classifier may be altered on demands, of which the present disclosure is not limited thereto.

At step S5 in FIG. 2, the segmentation result from the segmentation module 30 and the adipose tissue volume and calcium score extracted by the extraction module 40 is organized by the output module 50 for generation of an analysis result. In the embodiments described herein, the output module 50 is further configured to calculate a cardiovascular risk prediction score (a probability of survival) based on information analyzed in previous processing steps (steps S1-S4) of the system 1. Referring to FIG. 9, an example of report of the analysis result produced by the output module 50 is disclosed, where an original picture 501 of medical image of a subject, a segmenting result 502 of segmented regions (produced by the segmentation module 30) from the original picture 501, a result 503 regarding the quantification value (calculated by the extraction module 40) from the segmenting result 502, and a survival analysis 504 regarding the cardiovascular risk prediction score of the subject are presented. It should be noted that the format of the analysis result is not limited to the report as shown but can also presented in any suitable physical or virtual forms.

In the embodiments described herein, the formula for cardiovascular risk prediction score is built on research samples of patients underwent chest computed tomography scanning from a National Health Insurance Database through steps of: collecting the research samples from a total of 1970 patients, where the research sample comprises data of image information, outpatient information, hospitalization information, medication information, surrender (death) record, etc., of the patients; concatenating the research sample to launch a generation tracking research on said patients, which is about 2633.2 person-year; collecting (e.g., having the image information run through the machine learning model of the segmentation module 30 beforehand or collect records already labeled by clinicians on the image information from the National Health Insurance Database) the calcium score of the heart, ascending aorta, and descending aorta and the adipose tissue volume from the image information of the research samples; collecting a basic demography information (e.g., gender, age, etc.) and comorbidity information (about 57 items of comorbidity are defined) from the outpatient information, the hospitalization information and the medication information of the research samples; smoothing continuous variables (e.g., age, calcium score, etc.) from the information collected via a restricted cubic spline; and building the formula for the cardiovascular risk prediction score using Cox regression based on the smoothed continuous variables. As seen from FIG. 9, the cardiovascular risk prediction score is presented in a probability of a subject suffering an event (e.g., re-hospitalization or mortality) in terms of years counting from creation date of the report.

Figure 10:
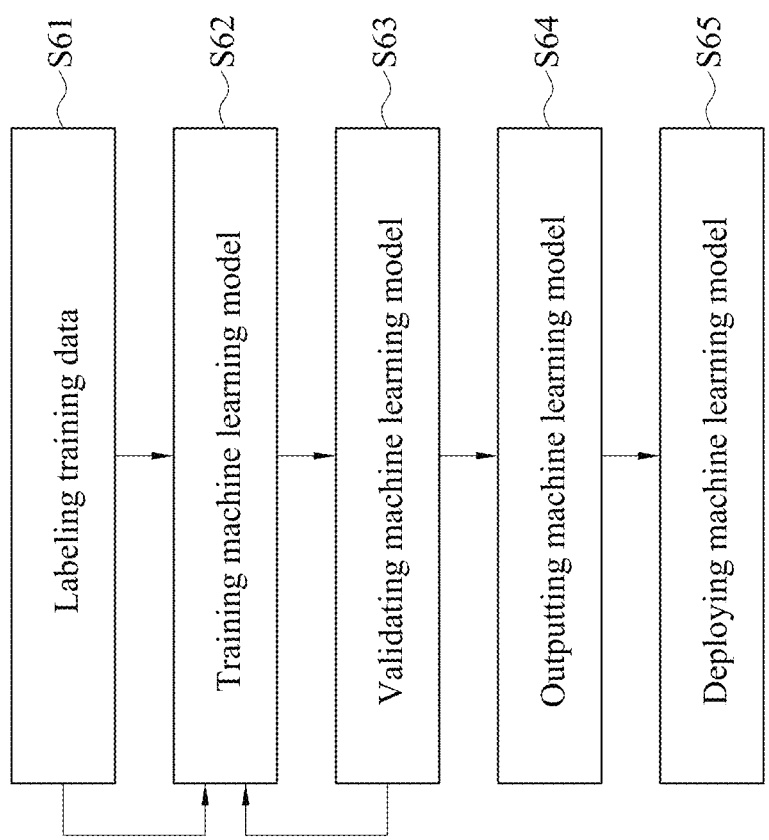
FIG. 10 is a flow chart illustrating steps for training a machine learning model in accordance with the present disclosure.

Referring to FIG. 10, a flow chart describing steps for training the machine learning model of the segmentation module 30 performed by the model training module 60 is disclosed, where FIGS. 11, 12A-1 to 12D-3, 13A to 13G-2, and 14 are also cited to illustrate execution details for each step by reference. It should be understood that the training of the machine learning model may operate independent of other elements of the system 1 (i.e., the steps S1 to S5 as shown in FIG. 2), and thus will not interfere operation of the system 1 during practical use.

In the embodiments described herein, the training of the machine learning model may be realized in any suitable developing platform such as NVIDIA DGX, NVIDIA EGX, TensorFlow, Caffe, or the like, and may utilize any suitable frameworks such as NVIDIA Clara imaging, Horovod, etc., of which the present disclosure is not limited thereto. In some embodiments, each step described in FIG. 10 may be realized by separate units or appointed units disposed within the model training module 60, of which the present disclosure is not limited thereto. In other embodiments, the model training module 60 is also configured to provide a GUI or other indication mechanism to guide user through steps described in FIG. 10, of which the present disclosure is also not limited thereto.

In at least one embodiment, the training of the machine learning model is performed on a basis of the federated learning. In general, it is difficult to collect huge amount of medical data for training a powerful neural network under restriction of privacy preservation, and data sharing between multiple medical institutions (e.g., hospitals) is usually infeasible. Therefore, the federated learning solves the above problems by decentralizing neural network training in each medical institution while only sharing training weights among said medical institutions to complete training of the machine learning model.

Figure 11:
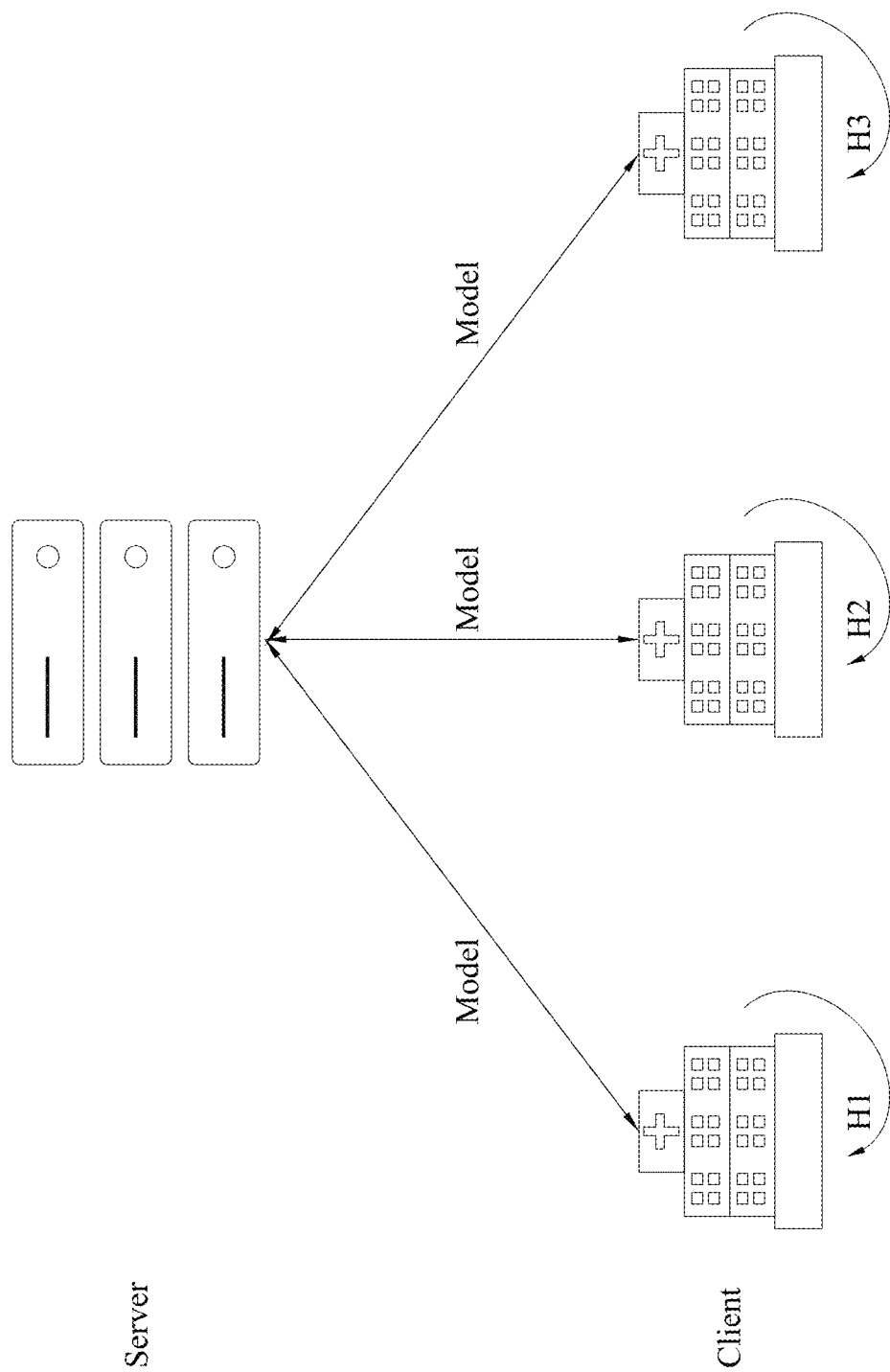
FIG. 11 is a schematic diagram illustrating the concept of the federated learning.

In the embodiments described herein, as shown in FIG. 11, three hospitals (denote as H1, H2, and H3, respectively) have participated in developing of the machine learning model of the segmentation module 30, and the federated learning thus will develop a relationship between a server side (developer) and client side (hospitals) for training of the machine learning model.

As shown in FIG. 11, the server side will first distribute initialized/pre-trained global weights to the client side. Then, hospitals of the client side will respectively train a local model based on the global weights using the patient data in corresponding hospitals H1/H2/H3. Next, local weights derived from the client side during training of the local model will be applied with differential privacy (e.g., techniques such as selective parameter sharing, sparse vector technique, etc.) to protect against model conversion before being returned to the server side. Finally, the client side will return the local weights to the server side, while the server side will aggregate the local weights by their contributions (e.g., the contributions are decided by data amount provided by each of the hospitals) as updated global weights for training of the machine learning model. After the training is complete, the updated global weights may be distributed to the client side again for deploying the machine learning model in practical use.

Based on the the concept of the federated learning as explained in FIG. 11, the steps for training the machine learning model of the segmentation module 30 will be described as follows.

At step S61 in FIG. 10, training data for the machine learning model is labeled using either the AI-Assisted Annotation (AIAA) tool (such as NVIDIA Clara train SDK provided by the NVIDIA Clara imaging) or labeling tool (such as 3D slicer, Medical Imaging Interaction Toolkit (MITK), etc.). However, the tools for labeling the training data are not limited to those described herein and can be altered with other suitable tools on demand, of which the present disclosure is not limited thereto.

Moreover, under consideration of privacy preservation in the case of the federated learning, the non-contrast or contrast medical image may first be de-identified before selected for labeling, so as to remove any identifiers (such as but not limited to the name, address, birth date, date of hospitalization, date of discharge, date of death, phone number, fax number, e-mail address, social security number, medical record number, health insurance card number, certificate number, license number, car registration number, medical material product number, personal URL address, personal IP address, biometric data, full face image, or others) that may expose identity of the subject that contributes the medical image.

It should be noted that there can be more or less rules for selecting training data for the machine learning model, and those requirements described are only for exemplification, which should not be restrictive to the scope of the present disclosure.

In the embodiments described herein, the process of labeling the training data is illustrated in FIGS. 12A-1 to 12D-3 and 13A to 13G-2, where FIGS. 12A-1 to 12D-3 illustrate a process of manually labeling the pericardium from medical image of a particular subject, and FIGS. 13A to 13G-2 illustrate a process of manually labeling aorta from medical image of a particular subject.

Figures 1, 2, 3, 12A:
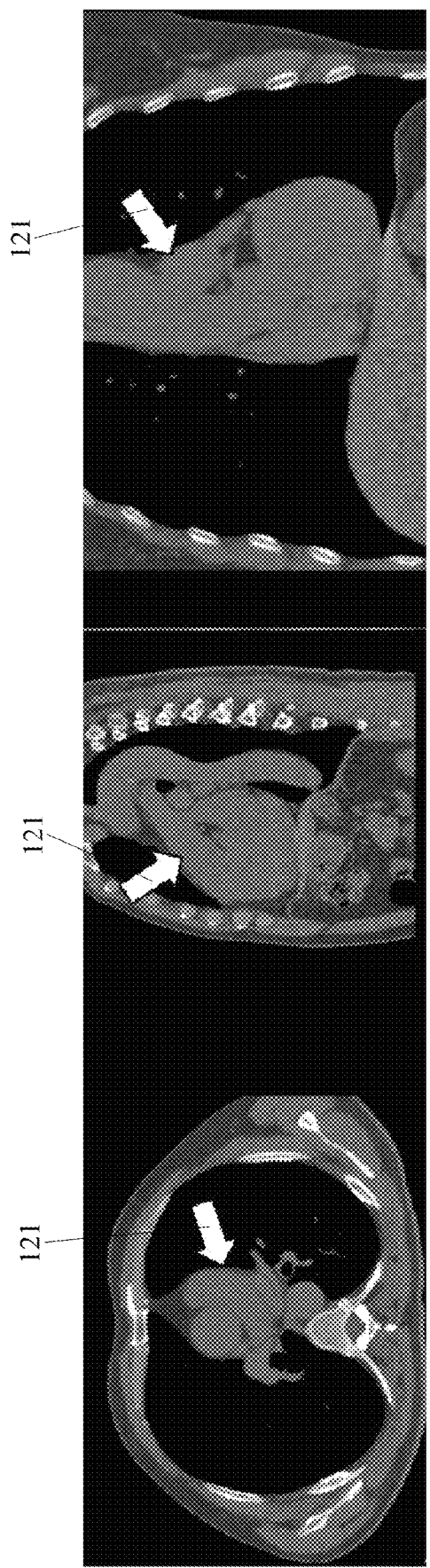

In the instance of manually labeling the pericardium of a particular subject from a medical image, the process is started by drawing the upper edge of the heart beginning from a starting point 121 of pulmonary trunk at base of the right ventricle. FIGS. 12A-1 to 12A-3 show the location of the starting point 121 for drawing the upper edge of the pericardium observed from the horizontal plane (FIG. 12A-1), sagittal plane (FIG. 12A-2), and coronal plane (FIG. 12A-3) of the subject, respectively, where the area of the upper edge observed from the starting point 121 at the horizontal plane (FIG. 12A-1) is subsequently circled. In this phase, caution is needed to not include esophagus into area of said upper edge of the pericardium.

Then, the process proceeds to drawing the lower edge of the pericardium that ends at apex 122 of the heart. FIGS. 12B-1 to 12B-3 show the location of the apex 122 for drawing the lower edge of the heart observed from the horizontal plane (FIG. 12B—1), sagittal plane (FIG. 12B-2), and coronal plane (FIG. 12B-3) of the subject, respectively, where area of the lower edge observed from the apex 122 at the horizontal plane (FIG. 12B-1) is subsequently circled. In this phase, caution is needed to not include liver into area of said lower edge of the pericardium.

Figures 1, 2, 3, 12C:
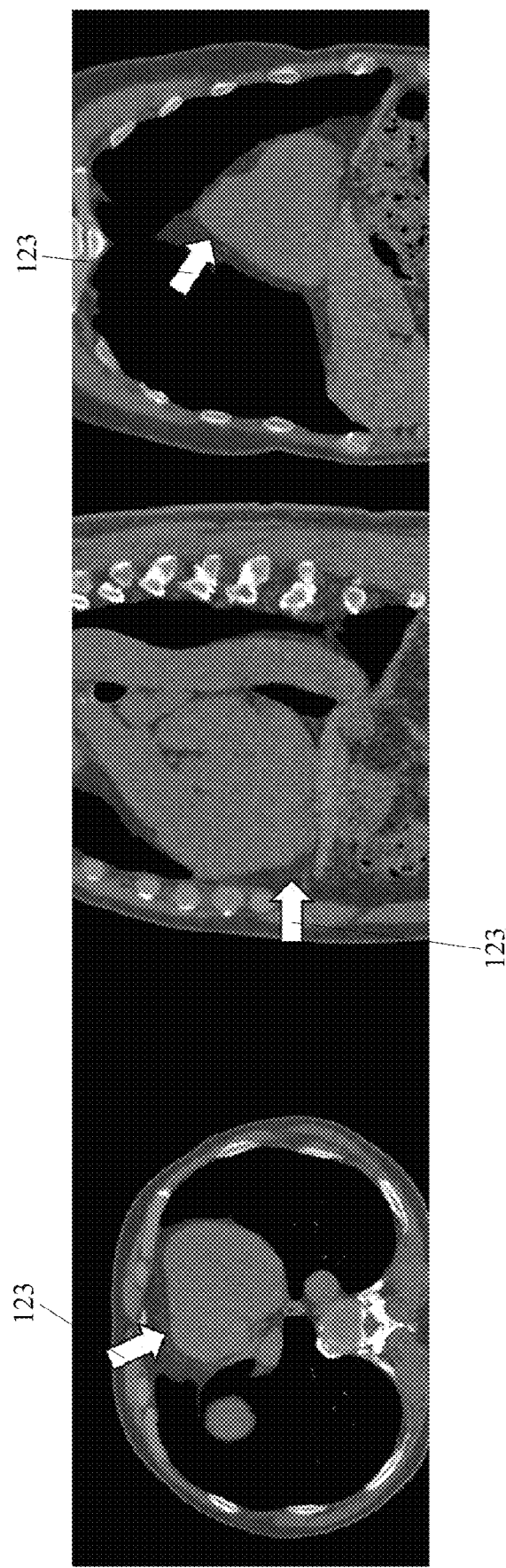

Next, the process is ended by drawing the border (connecting the upper edge and the lower edge) of the heart along pericardium 123 of the heart. FIGS. 12C-1 to 12C-3 show the location of the pericardium 123 for drawing from the horizontal plane (FIG. 12C-1), sagittal plane (FIG. 12C-2), and coronal plane (FIG. 12C-3) of the subject, respectively. In this phase, caution is needed to not include sternum into area of said border of the heart.

Figures 1, 2, 3, 12D:

FIGS. 12D-1 to 12D-3 show an example illustrating a heart and pericardium of a subject after the labeling is completed, where a circled area of the heart is shown on the horizontal plane (FIG. 12D-1), sagittal plane (FIG. 12D-2), and coronal plane (FIG. 12D-3) of the subject, respectively. From here, a smoothing function may be additionally applied to level out roughness of the area circled before being used as training data.

Figure 13A:
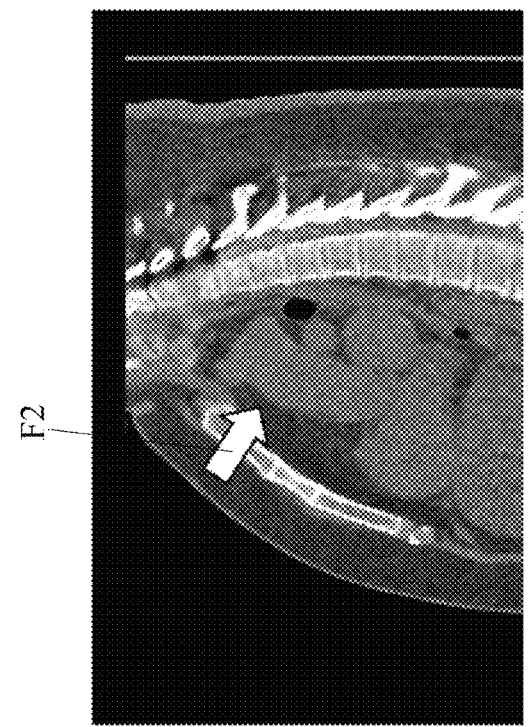

In the instance of manually labeling aorta of a particular subject from an image, the process is started by determining a fiducial point F2 of the aorta that intersects with brachiocephalic artery. FIG. 13A shows a location of the fiducial point F2 observed from sagittal plane of the subject.

Figure 13B:
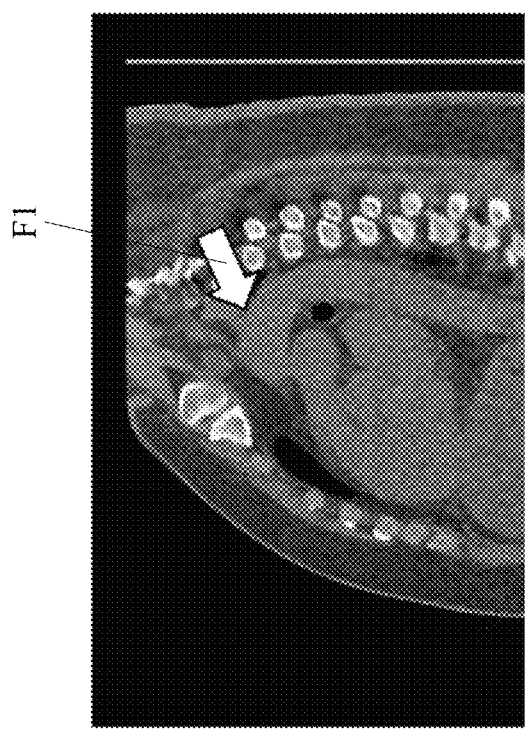

Then, the process proceeds to determining another fiducial point F1 of the aorta that intersects with the left subclavian artery. FIG. 13B shows a location of the fiducial point F1 observed from the sagittal plane of the subject.

Figures 1, 2, 3, 13C:
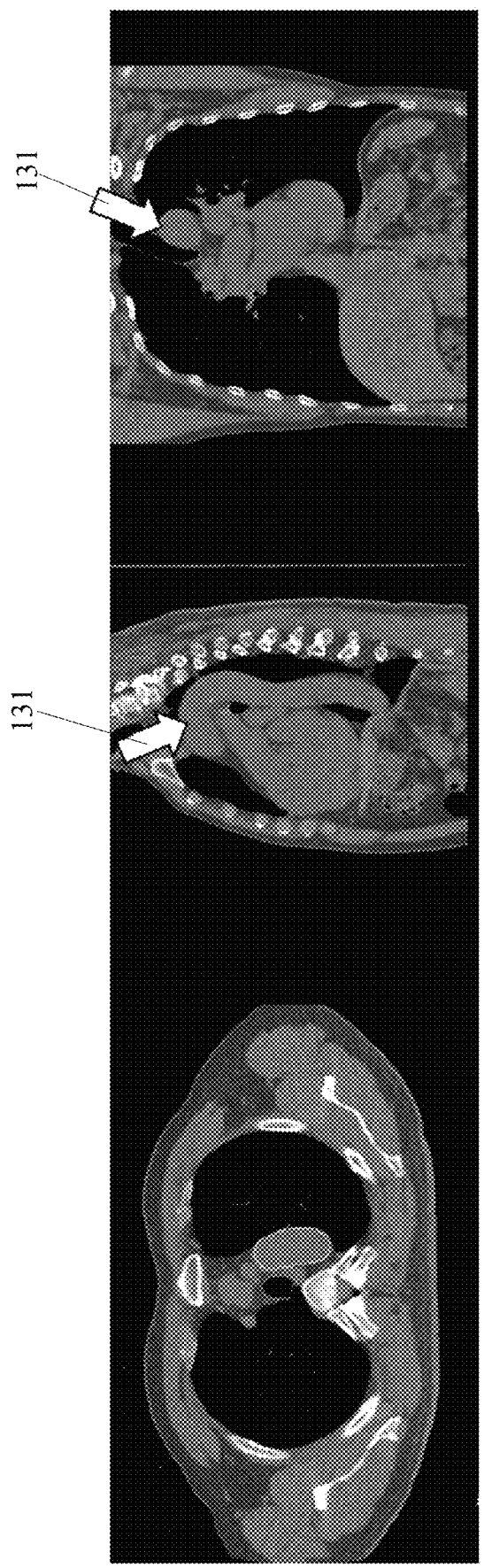

Next, the process proceeds to drawing the edge 131 of the arch of aorta. FIGS. 13C-1 to 13C-3 show the location for drawing the edge 131 of the arch of aorta observed from the horizontal plane (FIG. 13C-1), sagittal plane (FIG. 13C-2), and coronal plane (FIG. 13C-3) of the subject, respectively.

Figures 1, 2, 3, 13D:
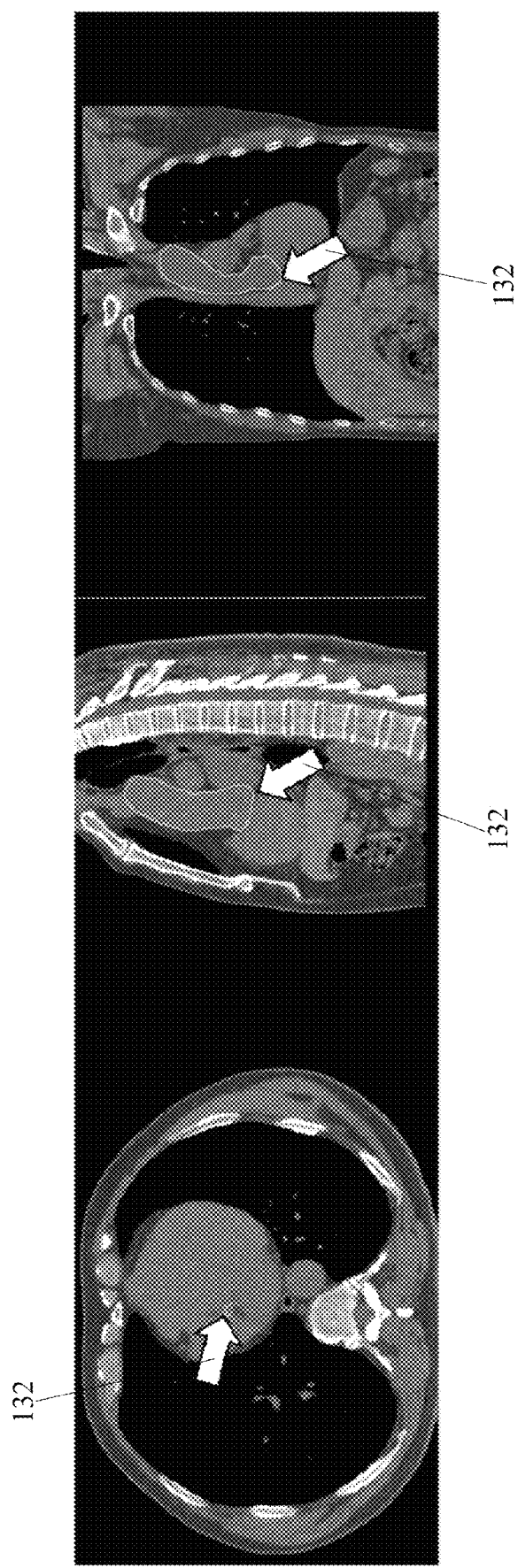

Further, the process proceeds to drawing the edge 132 of the ascending aorta. FIGS. 13D-1 to 13D-3 show the location for drawing the edge 132 of the ascending aorta observed from the horizontal plane (FIG. 13D-1), sagittal plane (FIG. 13D-2), and coronal plane (FIG. 13D-3) of the subject, respectively.

Figure 13E:
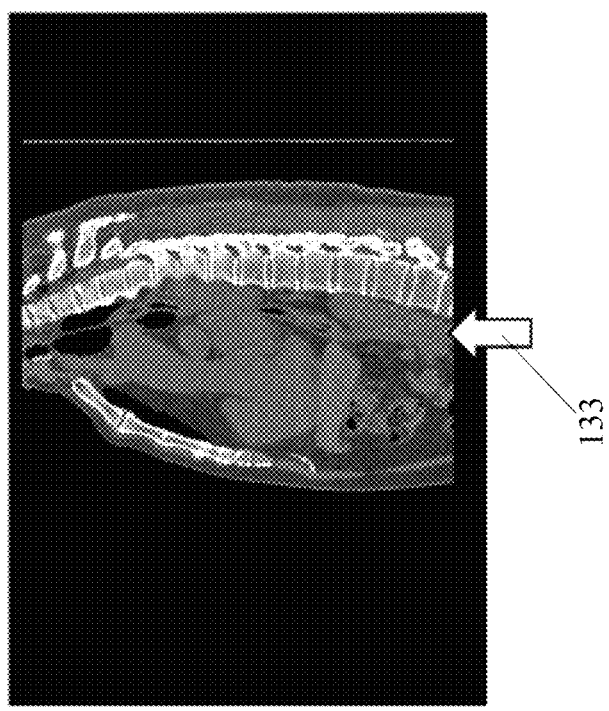

Then, the process proceeds to labeling the edge 133 of the descending aorta following the similar procedures as described in FIGS. 13C-1 to 13D-3, which is not further illustrated herein. FIG. 13E is included to illustrate an example of the edge 133 of the descending aorta after labeling that is observed from the sagittal plane of the subject, where the border of the descending aorta ends (see the lower boarder of the edge of the descending aorta) above the common iliac artery.

Figure 13F:
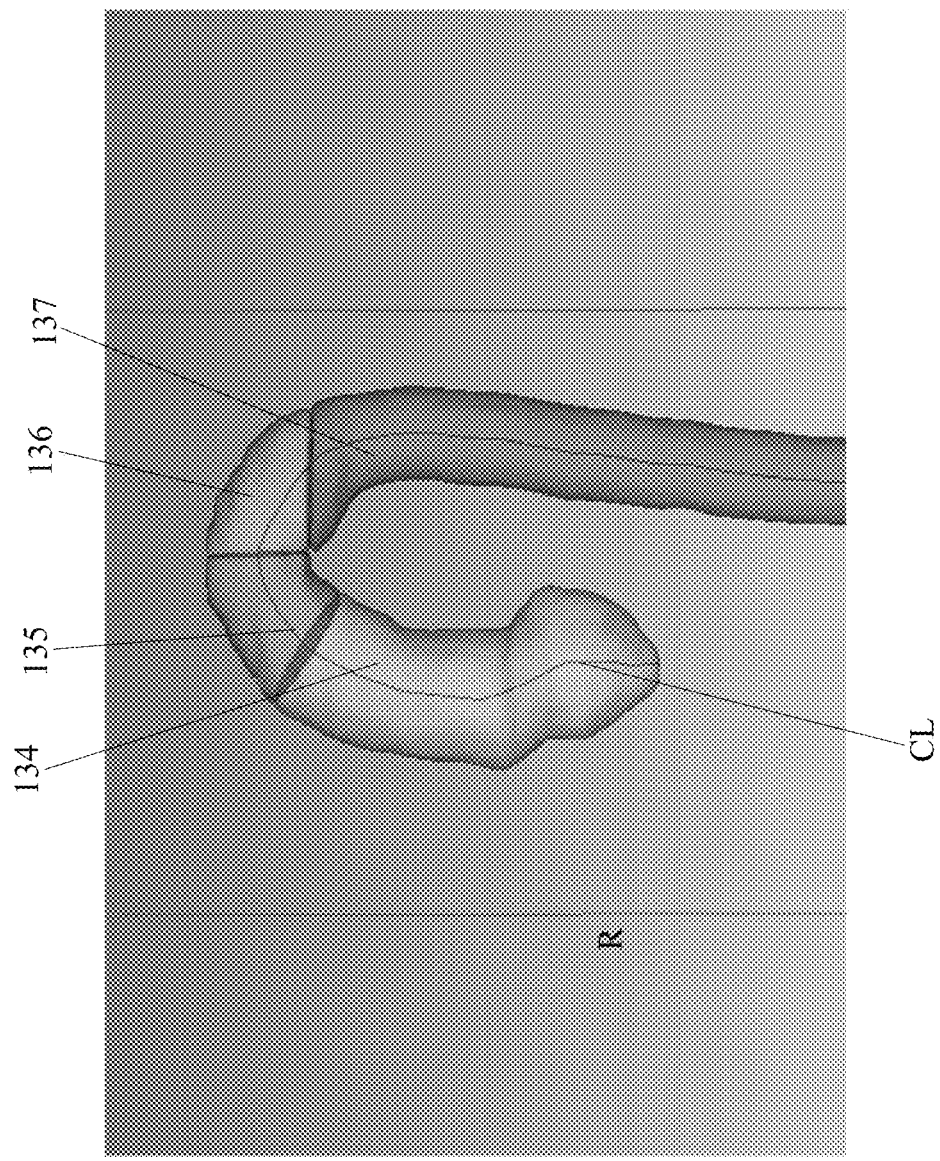

Next, the process proceeds to extracting centerline CL (via extraction function of the 3D slicer) from the determined edges of the aorta, so as to ensure the precise labeling of the aorta. FIG. 13F shows the centerline CL being extracted and its relationship with the ascending aorta 134, the aorta arch 135, the first descending aorta 136, and the second descending aorta 137 in a 3D view. Specifically, the process proceeds to determining the sections of the aorta is based on the above-mentioned fiducial points F1 and F2, where a section of the aorta between the heart (aortic root), and the fiducial point F2 is defined as the ascending aorta 134, a section of the aorta between the fiducial points F1 and F2 is defined as the aorta arch 135, a section of the aorta descend from the fiducial point F1 down to another end (away from the aortic root) of the aorta at a corresponding height of the fiducial point F2 (aorta will seem separated when observed from horizontal plane at this height of fiducial point F2) is defined as the first descending aorta 136, and the remaining section of the aorta is defined as the second descending aorta 137.

Figures 1, 2, 13G:
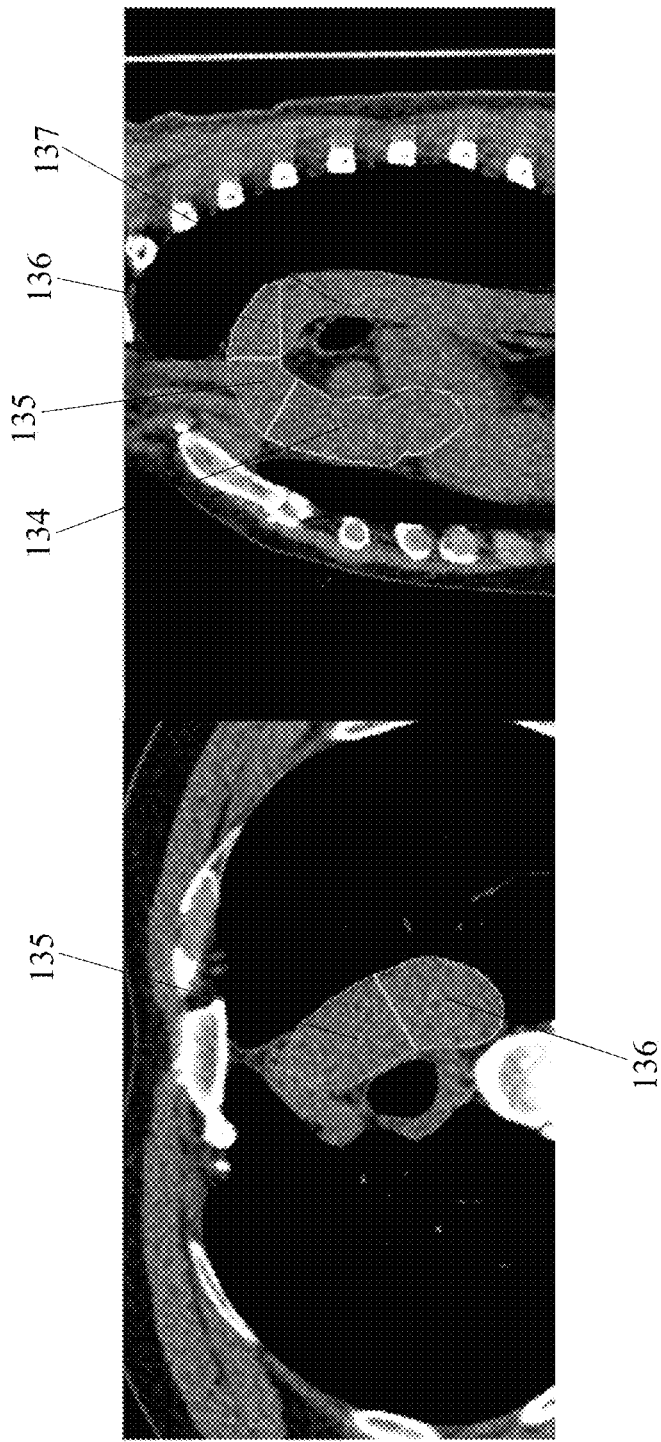

FIGS. 13G-1 and 13G-2 further show an example of the location of the ascending aorta 134, the aortic arch 135, the first descending aorta 136, and the second descending aorta 137 observed from the horizontal plane (FIG. 13G-1) and sagittal plane (FIG. 13G-2) of the subject, respectively.

After labeling of the aorta of the subject, a smoothing function may be applied to level out roughness of the area circled before being used as training data.

In the embodiments described herein, under the aim to collect adequate amount of training data, a more detailed process of labeling the training data comprises the steps of (see the relationship between steps S61 and S62 in FIG. 10): manually labeling (via 3D slicer) 10 instances of medical image (see the process described in FIGS. 12A-1 to 12D-3 and 13A to 13G-2); training a first version of the machine learning model based on said 10 instances of the medical image; using the first version of the machine learning model to act as an auxiliary annotation model for the AIAA tool to assist in manually labeling more medical images; training a second version of the machine learning model based on more medical images; repeating said labeling through manual labeling and the auxiliary annotation model and said training the second version of the machine learning model until training data is enough.

Figure 14:
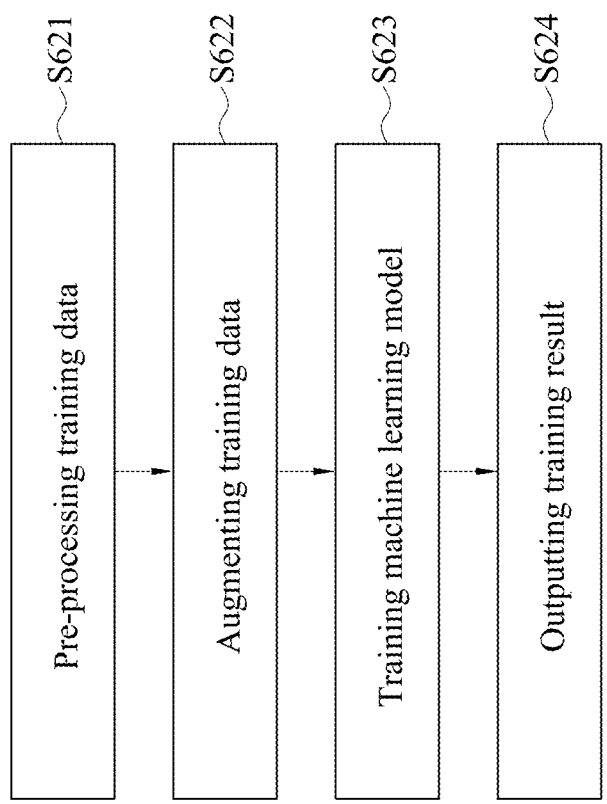
FIG. 14 is a flow chart illustrating steps for training a machine learning model in accordance with the present disclosure.

At step S62 in FIG. 10, the machine learning model (the second version of the machine learning model) is trained using the training data. FIG. 14 shows a flow chart of steps for training the machine learning model, which are described hereinafter.

At step S621, the training data is pre-processed into a predetermined consistency by performing resampling, normalizing, and converting on the training data. The pre-processing of the training data has a similar procedure to those described in the pre-processing module 20 as mentioned above, hence will not be further described herein.

At step S622, the training data will further be augmented to prevent overfitting. In the embodiments described herein, the 3D volume of the medical image pre-processed from the training data may first be randomly cropped into a random size (e.g., maximum with 160×160×160 pixels and/or minimum with 64×64×64 pixels). Then, the randomly cropped 3D volume of the medical image may be padded with a fixed size (e.g., 160×160×160 pixels) to ensure smooth training for the machine learning model. Other augmentation techniques may also be utilized herein, such as but not limited to: processing the 3D volume of the medical image with random spatial flipping augmentation to increase variance of the training data, scaling or shifting intensity of the 3D volume of the medical image without background to regularize the machine learning model during training. Therefore, even if the scanning devices from different hospitals have different imaging capabilities, the machine learning model may still be generalized to process various types of the medical images as training data.

At step S623, the training data is sent to the machine learning model for training. It should be noted that the network architecture of the machine learning model during training is the same as those described in FIGS. 4A and 4B, and thus will not be further detailed.

At step S624, a training result of the machine learning model (e.g., a segmentation result output by the machine learning model during training) will be output for validation in later processing.

Continue on step S63 of FIG. 10, the machine learning model being trained is put under validation to quantify its segmentation performance (based on the training result from step S624 in FIG. 14). In the embodiments described herein, a loss function is utilized to validate the segmentation performance of the machine learning model, which can be expressed as a dice loss designed from dice similarity coefficient (DSC) defined as follows:

$$DSC = \frac{2|y \cap \hat{y}|}{|y| + |\hat{y}|},$$

Dice Loss = 1 − DSC where y denotes target region for the machine learning model to segment (i.e., the regions of heart/pericardium and aorta labeled in the training data), and ŷ denotes predicted region actually segmented by the machine learning model during training.

From the above, it can be understood that the DSC aims to measure similarity of target region and predicted region identified by the machine learning model, thus is a quantifiable measure to evaluate segmentation performance of the machine learning model.

Based on the loss function, the model training module 60 may put the machine learning model back to training (see the relationship between steps S63 and S62 in FIG. 10) or get the machine learning model ready for practical use (i.e., proceeding to step S64 in FIG. 10). In the embodiments described herein, the machine learning model should at least reach the DSC listed in Table 2 below before being put for practical use.

TABLE 2

Training results of the machine learning model

| Target Region | DSC of segmentation after training |
| --- | --- |
| Heart/Pericardium | 0.948 ± 0.013 |
| Ascending Aorta | 0.925 ± 0.012 |
| Descending Aorta | 0.901 ± 0.023 |

The machine learning model with adequate segmentation performance will be output at step S64 and deployed (e.g., via NVIDIA Clara deploy SDK provided by NVIDIA Clara Imaging) to the segmentation module 30 at step S65 at the end of the training. If the machine learning model is first deployed to the segmentation module 30, elements of the system 1 may hence put into practical use for cardiovascular risk prediction of arbitrary subject at real-time. However, the model training module 60 may still operate to optimize performance of the machine learning model of the segmentation module 30 based on updated training data and/or parameter settings during clinical practice in real-time.

In further embodiments described herein, a computer readable medium is also present, which stores a computer executable code, and the computer executable code is configured to realize the steps S1 to S5 of FIG. 2, steps S61 to S65 of FIG. 10, and/or steps S621 to S624 of FIG. 14 as discussed above after being executed.

In summary, the present disclosure utilizes artificial intelligence to perform segmentation on medical images to identify precise regions of the heart, aorta and/or pericardium of a subject, so as to derive the adipose tissue volume and calcium score from the non-contrast or contrast medical images for cardiovascular risk prediction.

What is claimed is:

1. A system for cardiovascular risk prediction, comprising:
   a segmentation module configured to segment a region from a medical image, wherein the segmentation module is implemented with a machine learning model to segment the region from the medical image, and wherein the machine learning model has a network architecture comprising an encoder part, a decoder part, an attention mechanism, and a variational auto-encoder decoder branch; and
   an extraction module configured to extract an analysis result from the region of the medical image, wherein the attention mechanism is configured to highlight salient features passed through skip connections between the encoder part and the decoder part, and wherein the variational auto-encoder decoder branch is configured to reconstruct the medical image based on features from endpoint of the encoder part during training of the machine learning model.

2. The system of claim 1, wherein the medical image is a non-contrast or contrast computed tomography image.

3. The system of claim 1, further comprising a model training module configured to provide training to the machine learning model through steps of:
   pre-processing a training data into a predetermined consistency;
   augmenting the training data by performing random cropping, random spatial flipping and/or random scaling or shifting of intensity on the training data;
   training the machine learning model using the training data; and
   validating a training result of the machine learning model using a loss function.

4. The system of claim 3, wherein the training data is generated via labeling the medical image manually and/or with assistance of an auxiliary annotation model.

5. The system of claim 1, wherein the analysis result comprises an adipose tissue volume of the region, and wherein the extraction module comprises a fat extraction unit configured to quantify the adipose tissue volume within the pericardium in the region through steps of:
   calculating a Hounsfield unit value for the pericardium based on an attenuation coefficient under computed tomography;
   defining a range of positive and negative standard deviation for the Hounsfield unit value on a basis of noise tolerance; and
   determining the adipose tissue volume within the pericardium based on the range.

6. The system of claim 1, wherein the analysis result comprises a calcium score of the region, and wherein the extraction module comprises a calcium extraction unit configured to quantify the calcium score of a heart or an aorta from the region through steps of:
   identifying a calcium region from the region based on a cut point defined by an Agatston score;
   capturing the calcium regions as a 3D image;
   analyzing the 3D image by a classifier to determine a classification of the calcium region;
   assigning a calcium score for the calcium region; and
   generating a heatmap to illustrate the calcium region and the calcium score.

7. The system of claim 1, further comprising a pre-processing module configured to pre-process the medical image into a predetermined consistency through steps of:
   resampling a 3D volume of the medical image into a spacing of 2×2×2 mm or any predetermined size; and
   normalizing an intensity of the 3D volume into unit standard deviation with zero mean.

8. The system of claim 1, further comprising an output module configured to present a cardiovascular risk prediction score based on the analysis result.

9. A method for cardiovascular risk prediction, comprising:
   segmenting a region from a medical image by a segmentation module, wherein the segmentation module is implemented with a machine learning model to segment the region from the medical image, and wherein the machine learning model has a network architecture comprising an encoder part, a decoder part, an attention mechanism, and a variational auto-encoder decoder branch; and
   extracting analysis result from the region of the medical image by an extraction module, wherein the attention mechanism is configured to highlight salient features passed through skip connections between the encoder part and the decoder part, and wherein the variational auto-encoder decoder branch is configured to reconstruct the medical image based on features from endpoint of the encoder part during training of the machine learning model.

10. The method of claim 9, wherein the medical image is a computed tomography image.

11. The method of claim 9, further comprising a model training module configured to provide training to the machine learning model through steps of:
   pre-processing a training data into a predetermined consistency, wherein the training data is generated via labeling the medical image manually and/or with assistance of an auxiliary annotation model;
   augmenting the training data by performing random cropping, random spatial flipping and/or random scaling or shifting of intensity on the training data;
   training the machine learning model using the training data; and
   validating a training result of the machine learning model using a loss function.

12. The method of claim 9, wherein the analysis result comprises an adipose tissue volume of the region, and wherein the extraction module comprises a fat extraction unit configured to quantify the adipose tissue volume within the pericardium in the region through steps of:
   calculating a Hounsfield unit value for the pericardium based on an attenuation coefficient under computed tomography;
   defining a range of positive and negative standard deviation for the Hounsfield unit value on a basis of noise tolerance; and determining the adipose tissue volume within the pericardium based on the range.

13. The method of claim 9, wherein the analysis result comprises a calcium score of the region, and wherein the extraction module comprises a calcium extraction unit configured to quantify the calcium score of a heart or an aorta from the region through steps of:
identifying a calcium region from the region based on a cut point defined by an Agatston score;
capturing the calcium regions as a 3D image;
analyzing the 3D image by a classifier to determine a classification of the calcium region;
assigning a calcium score for the calcium region; and
generating a heatmap to illustrate the calcium region and the calcium score.

14. The method of claim 9, further comprising a pre-processing module configured to pre-process the medical image into a predetermined consistency through steps of:
resampling a 3D volume of the medical image into a spacing of 2×2×2 mm or any predetermined size; and
normalizing an intensity of the 3D volume into unit standard deviation with zero mean.

15. The method of claim 9, further comprising an output module configured to present a cardiovascular risk prediction score based on the analysis result.

16. A non-transitory computer readable medium, which stores a computer executable code, the computer executable code implementing the method according to claim 1 after being executed.

* * * * *